(12) United States Patent
Lin et al.

(10) Patent No.: US 10,820,595 B2
(45) Date of Patent: Nov. 3, 2020

(54) BACILLUS AMYLOLIQUEFACIENS STRAIN AND ITS USE

(71) Applicant: National Pingtung University of Science and Technology, Neipu Township (TW)

(72) Inventors: Yi-Hsien Lin, Neipu Township (TW); Ting-Hsin Ho, Neipu Township (TW)

(73) Assignee: National Pingtung University of Science and Technology, Neipu Township (TW)

( * ) Notice: Subject to any disclaimer, the term of this patent is extended or adjusted under 35 U.S.C. 154(b) by 0 days.

(21) Appl. No.: 15/828,663

(22) Filed: Dec. 1, 2017

(65) Prior Publication Data

US 2019/0014785 A1 Jan. 17, 2019

(30) Foreign Application Priority Data

Jul. 13, 2017 (TW) .............................. 106123493 A

(51) Int. Cl.
| | | |
|---|---|---|
| *A01N 63/10* | (2020.01) | |
| *C12N 1/20* | (2006.01) | |
| *A23L 3/3571* | (2006.01) | |
| *C12R 1/07* | (2006.01) | |
| *A01N 63/00* | (2020.01) | |
| *A01N 63/22* | (2020.01) | |

(52) U.S. Cl.
CPC .............. *A01N 63/10* (2020.01); *A01N 63/00* (2013.01); *A01N 63/22* (2020.01); *A23L 3/3571* (2013.01); *C12N 1/20* (2013.01); *C12R 1/07* (2013.01)

(58) Field of Classification Search
CPC ........ A01N 63/02; A01N 63/10; A01N 63/22; A01N 63/00; A01N 63/38; A01N 63/40; A01N 63/34; A01N 63/25; A01N 63/23; A01N 63/60; A01N 63/12; A01N 63/16; A01N 63/28; A01N 63/36; A01N 63/30; A01N 65/03; A01N 63/50; A01N 63/32; A01N 63/20; A01N 63/27; A01N 63/14; C12N 1/20; A23L 3/3571; C12R 1/07
See application file for complete search history.

(56) References Cited

FOREIGN PATENT DOCUMENTS

| | | | |
|---|---|---|---|
| CN | 1792167 A | * | 6/2006 |
| KR | 20110120748 A | * | 11/2011 |

OTHER PUBLICATIONS

Hashimoto, N., JP2009247302, Novel Bacillus amyloliquefaciens strain 3K-4, useful in plant disease control agent for preventing damages to agriculture and horticulture crops caused by bacterial and fungal disease, e.g. cabbage black rot and citrus canker, 2009, Derwent Abstract, 3 pages (Year: 2009).*

Nam, et al., Bacillus amyloliquefaciens CP1 and Control Method of Strawberry anthracnose Using the Same, 2011, Translation, Google Patents, pp. 1-9. (Year: 2011).*

De Melo Pereira et al.; "A Multiphasic Approach for the Identification of Endophytic Bacterial in Strawberry Fruit and their Potential for Plant Growth Promotion"; Microb Ecol; 2012; pp. 405-417; vol. 63.

Han et al.; "The bacterial lipopeptide iturins induce Verticillium dahliae cell death by affecting fungal signalling pathways and mediate plant defence responses involved in pathogen-associated molecular pattern-triggered immunity"; Environmental Microbiology; 2015; pp. 1166-1188; vol. 17:4.

* cited by examiner

*Primary Examiner* — John Pak
*Assistant Examiner* — Andriae M Holt
(74) *Attorney, Agent, or Firm* — The Webb Law Firm

(57) ABSTRACT

Provided herein is *Bacillus amyloliquefaciens* strain PMB05 used in the field of plant disease control. Inoculation of plants with the strain can increase immune responses induced by detection of fungi and/or bacteria in plant, for example, increase the production of ROS and deposition of callose. Also, the strain has the effect of promoting plant growth. Therefore, the strain and its culture filtrate of the present invention can boost plant disease resistance and promote plant growth, which can be extensively used to control plant diseases and have the potential of turning into a commodified biological control agent.

7 Claims, 23 Drawing Sheets

Blank               200X

BACILLUS AMYLOLIQUEFACIENS STRAIN AND ITS USE

CROSS REFERENCE TO RELATED APPLICATION

This application claims priority to Taiwan Invention Patent Application No. 106123493 filed Jul. 13, 2017, the disclosure of which is hereby incorporated in its entirety by reference.

FIELD OF THE INVENTION

The invention relates to a *Bacillus amyloliquefaciens* strain used in the field of plant disease control. More specifically, the invention relates to a *Bacillus amyloliquefaciens* strain PMB05 obtained from selection (Deposit number of biological material: BCRC 910784).

BACKGROUND OF THE INVENTION

Plants are easily affected by plant diseases like bacterial and fungal infections in the growth process. At present, synthetic chemical compounds are widely used to control plant diseases. However, most chemical pesticides are also harmful to non-target organisms and continuous uses of pesticides are deleterious to human health or causing environmental pollution. Moreover, the pathogens might develop resistance to pesticides and plant diseases cannot be fully controlled. In the view of human health and environmental sustainability in recent years, there is an increasing need for biological control of diseases.

Biological control using antagonistic microorganisms separated from the nature has less effect on the environment, and can reduce the risk of pathogens resistance to pesticides. Some antagonistic microorganisms have been selected from the nature, for example, *Bacillus* spp., *Trichoderma* spp., *Pseudomonas* spp., *Streptomyces* spp. and the like. The disease control mechanism of antagonistic microorganisms includes antibiosis, competition, degrading enzymes secretion, induced resistance and the like.

In which, *Bacillus* spp. is Gram-positive antagonistic bacilli, can grow in room temperature and neutral pH environment, and has the characteristic of producing endospore. Therefore it is suitable in cultivation environment of crops, and it can withstand damages like high temperature, dryness and UV which has advantages in industrial application like mass production and storage. As an actual example of antagonistic microorganism, it is known that *Bacillus circulars* IAM 1165 strain can secrete fungi cell wall degrading enzymes; *Bacillus subtilis* secretes cyclic lipopeptide compound that can inhibit the growth of various plant pathogens; and studies show that *Bacillus amyloliquefaciens* strain S13-3 can facilitate the production of plant PR proteins like chitinase.

However, the application of *Bacillus* spp. in the aforementioned disease control examples has disadvantages like unstable control efficacies against diseases and limitation of type of diseases to be applied because of the latent infection and mutation of pathogens.

In plant immune responses, the process of receptors on plant cell membrane identifying pathogen-associated molecular patterns (PAMPs) and activating defensive responses are called PTI (PAMP triggered immunity). PTI originates from the cell membrane and is the first line of defence when fighting against plant diseases. If an antagonistic microorganism can strengthen this PTI defence response, that microorganism can be extensively used to control multiple plant diseases.

In the process of PTI, production of reactive oxygen species (ROS) and callose deposition are crucial to fight against infection with pathogens. The former leads to the programmed death of infected cells, and induce defence-related genes expression; whereas the latter one occurs between plant cell membrane and cell wall, and can strengthen the cell wall to prevent pathogens attack. These two are the important indicator signals of plant immune response. As is known from the previous studies, iturins produced by *Bacillus amyloliquefaciens* strain 41B-1 can reinforce cotton to produce ROS and callose, thus preventing cotton *Verticillium* wilt which is caused by fungal pathogens. However, the *Bacillus* spp. that can enhance PTI immune response after detection of bacterial pathogens in plant is not disclosed by the relevant art.

Furthermore in agricultural management, in order to increase production output and reduce the losses caused by plant diseases, there is a need for promoting plant growth. Yet there would be problems like pesticides residues if chemical fertilisers are used. Therefore, an antagonistic microorganism that can also promote plant growth is expected in the development of biological control. In the previous studies, *Bacillus subtilis* in endophyte of strawberries can promote the growth of strawberries plant. As for whether *Bacillus amyloliquefaciens* strain can also improve immune response and promote plant growth, it is not disclosed by the relevant art.

RELATED BACKGROUND ART OF THE INVENTION

Non-Patent Documents

Han, Q., Wu, F., Wang, X., Qi, H., Shi, L., Ren, A., Liu, Q., Zhao, M., and Tang, C. 2014. The bacterial lipopeptide iturins induce *Verticillium dahliae* cell death by affecting fungal signalling pathways and mediate plant defence responses involved in pathogen-associated molecular pattern-triggered immunity. Environ. Microbiol. 17: 1166-1188.

de Melo Pereira, G. V., Magalhães, K. T., Lorenzetii, E. R., Souza, T. P., and Schwan, R. F. 2012. A multiphasic approach for the identification of endophytic bacterial in strawberry fruit and their potential for plant growth promotion. Microb. Ecol. 63: 405-417.

SUMMARY OF THE INVENTION

The present application of *Bacillus* spp. in the aforementioned disease control examples has disadvantages like unstable control efficacies against diseases and limitation of type of diseases to be applied because of the latent infection and mutation of pathogens. In addition, an antagonistic microorganism that can also promote plant growth is expected in the development of microbial control of plant diseases.

Hence, this invention aims at providing a *Bacillus* spp. strain that can strengthen PTI defence response in plant and can be extensively used to control multiple plant diseases. Besides, that *Bacillus* spp. strain has the effect of promoting plant growth.

The inventors of the present invention carry out in-depth studies in view of the foresaid issues and successfully select *Bacillus amyloliquefaciens* strain PMB05. As shown in FIG. 28, it can increase the immune responses which are induced by the detection of fungi and/or bacteria in plant, for example, increase the production of ROS and deposition of callose, which could boost plant disease resistance. On the other hand, that strain has the effect of promoting plant growth.

Accordingly, this invention provides a *Bacillus amyloliquefaciens* strain, strain PMB05, which is deposited in Food Industry Research and Development Institute, Hsinchu City, Taiwan, under the deposition number of biological material BCRC 910784 and the date of deposition is Jul. 4, 2017. The *Bacillus amyloliquefaciens* strain, strain PMB05, described herein was also deposited under the Budapest Treaty with the China Center for Type Culture Collection, Wuhan University, Wuhan 430072, People's Republic of China, under Accession No. CCTCC M 2018075, on Jan. 24, 2018.

The aforesaid strain PMB05 can increase immune responses of plants which are induced by the detection of fungi and/or bacteria in plant. And, the aforesaid immune responses are production of ROS, deposition of callose and the like.

Moreover, the present invention provides a microbial agent, comprising culture filtrate and/or cell suspension of *Bacillus amyloliquefaciens* strain PMB05, as active ingredients.

The said strain PMB05 can be used to prevent and cure plant diseases that are caused by fungi and/or bacteria. Wherein, the foresaid fungi at least include strawberry anthracnose fungi (*C. gloeosporioides*); the foresaid bacteria at least include bacteria of bacterial fruit blotch (*Acidovorax citrulli*), bacteria of citrus bacterial canker (*Xanthomonas citri* subsp. *citri*), and bacteria of bacterial soft rot (*Pectobacterium carotovorum* subsp. *carotovorum*).

The foresaid strain PMB05 can be also used to promote plant growth.

The strain of the invention can increase the immune responses induced by the plants after detection of fungi and/or bacteria in plant, specifically, increase the production of ROS and deposition of callose, which could boost plant disease resistance. That strain is effective in controlling diseases caused by fungi and bacteria, and can be extensively used to control various plant diseases. When the strain is used on a plant, it has the effect of promoting plant growth.

DETAILED DESCRIPTION OF THE INVENTION

Figure 1:
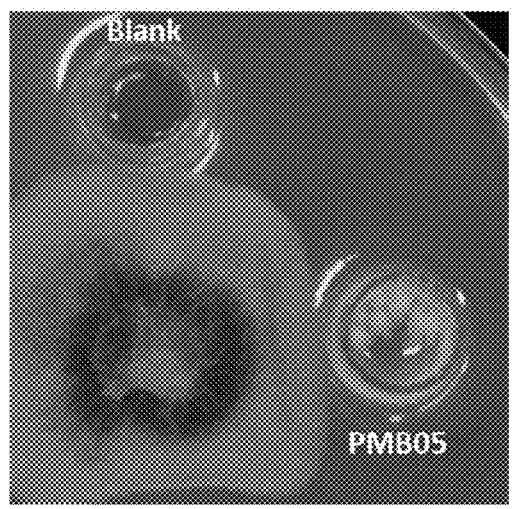
FIG. 1 shows the result of dual cultural test of strain PMB05 against strawberry anthracnose.

The present invention will be further exemplified by the following examples, which are not to be seen as limiting. The embodiments and description are used for illustrating the details and effect of the present invention.

[Source and Cultivation of the Strain]

This strain PMB05 (*Bacillus amyloliquefaciens* strain PMB05) is collected from rhizosphere of plant in National Pingtung University of Science and Technology Experimental Farm, and undergoes incubation and selection. Serial dilution using a soil-to-water ratio of 9:1 is performed on the collected soil, and the sample is put in water bath of 60° C.

for 30 minutes. After that, sample of 100 µl is suctioned and cultured in a solid culture medium of nutrient agar (NA). After the plates are incubated at 28° C. in the incubator for 24-28 hours, colonies that are similar to Bacillus spp. (light grey, opaque and have rough surfaces) are selected and cultured in a NA solid culture medium for a pure-culture process. After incubated at 28° C. in the incubator for 24-28 hours, 3% potassium hydroxide (KOH) is used for the initial screening of Gram-positive bacteria. The purified strains are preserved in a 20% glycerine solution by cryopreservation.

[Identification of Strain]

The strain of Bacillus spp. is identified by the sequence of 16SrDNA and gyrB gene. For the amplification of gene sequence, 16S rDNA and gyrB are amplified with specific gene primers 27-F/1525-R and UP-1/UP-2r respectively (Wawrik et al., 2005), and the colonies are PCR-amplified with Kapa2G™ Fast PCR Kit (Kapa biosystems, USA) directly. The products from amplification are then cloned with pGMT-T cloning kit (GeneMark, Taiwan). After confirming the strain contains the cloning target sequence, the cloned strain is sent to Genomics (Taiwan) for sequencing. The gene sequencing results of 16S rDNA and gyrB are thereafter aligned by the BLAST tool on NCBI website and SepsiTest™ Blast.

The alignment results are shown in CHART 1, the identities between the 16S rDNA gene sequence of PMB05 and 3 published sequences of B. amyloliquefaciens strains is 99.0%; whereas the identities between the 16S rDNA gene sequence of PMB05 and 3 published sequences of B. subtilis strains is 98.7%-98.8%, hence PMB05 is more similar to Bacillus amyloliquefaciens. The SepsiTest™ alignment results also show the gene sequence of 16S rDNA of PMB05 is most similar to Bacillus amyloliquefaciens, and the identities is 99.2%.

Similarly in the identification of gyrB gene sequence, the alignment results of BLAST conducted on NCBI are shown in CHART 2. The identities between PMB05 and 3 published sequences of B. amyloliquefaciens strains is 98.0%-98.5% (CHART 2), whereas the identities between PMB05 and 3 published sequences of B. subtilis is 95.0%-98.0%. According to the above results, PMB05 is identified as Bacillus amyloliquefaciens.

[Preparation of the Strain Cell Suspension]

In order to analyse the impact of PMB05 against pathogen growth and plant immune response, the strain cell suspension is prepared by the following method. Place PMB05 on NA culture medium (nutrient broth 8 g/L and agar 5 g/L) and incubate at 28° C. for 48 hours. Then pick a single colony to NB liquid culture medium (nutrient broth 8 g/L), incubate at 37° C. for 16 hours with shaking at 150 rpm. After that, centrifuge it at 5500×g and 24° C. for 3-5 minutes. Let PMB05 fungus bodies precipitate in the 50 ml centrifuge tube, and remove the supernatant and add sterile $H_2O$ to suspend the cultured precipitate again. Measure the concentration by spectrophotometer, and the OD600 value should be approximately 0.3. The preparation of cell suspension is now finished.

[Preparation of the Strain Culture Filtrate]

In order to analyse the impact of non-viable ingredients in the PMB05 culture liquid against pathogen growth and plant immune response, the strain culture filtrate is prepared by the following method. First, pick a single colony from PMB05 antagonistic bacteria and transfer it to NB (nutrient broth 8 g/L) liquid culture medium, incubate at 37° C. for 16 hours with shaking at 150 rpm. Then, centrifuge it at 5500×g and 24° C. for 3-5 minutes. Let PMB05 fungus bodies precipitate in the 50 ml centrifuge tube, remove the supernatant and add sterile $H_2O$ to suspend the precipitate again. Measure the concentration by spectrophotometer (CT2800 Spectrophotometer, Taiwan) until the 00600 value is approximately 0.3. Then transfer 1 ml of the foresaid suspended culture to a 50 ml conical flask containing 10 ml of 523 culture medium (each liter contains 10 g of sucrose, 8 g of casein dehydrolysate, 4 g of yeast extract, 2 g of $KH_2PO_4$ and 0.3 g of $MgSO_4$, pH 7.0), and incubate with shaking at 30° C., 150 rpm for 8 hours. Next, adjust the culture fluid to the OD600 value 0.3 for the inoculum. Transfer 1 ml of the adjusted fluid to a 500 ml conical flask containing 100 ml of SYM culture medium (each liter contains 20 g of dark brown sugar, 10 g of soy flour, 5 g of yeast powder, 1.6 g of $K_2HPO_4$, 0.8 g of $KH_2PO_4$ and 0.3 g of $MgSO_4$, pH 7.5), and incubate with shaking at 30° C., 150 rpm for 5 days. Finally, centrifuge the culture at 5500×g for 5 minutes. Collect the supernatant and filter it by passing it through a 0.22 µm membrane filter (Sterile Syringe Filter). After that, collect the filtrate and freeze it in the refrigerator at 4° C.

[Preparation of the Strain Fermentation Liquid]

Prepare a 10 L fermentation tank and dissolve 0.5% yeast, 1.5% molasses, 0.5% soy protein, 0.1% $K_2HPO_4$ and 0.1% $KH_2PO_4$ in total volume of 7 L of distilled water. Add the formulation to the tank, sterilize in sterilizer at 121° C. for 50 minutes and the sterile fermentation medium is obtained. After cooling the fermentation medium, set the fermentation system to 30° C. and 200 rpm and then 100 ml of PMB05 culture liquid (adjust the concentration of nutrient broth culture medium to OD600 value 0.3) is added to the fermentation tank, and incubate for 6 days continuously. Bacteria count is conducted every two days and when the bacteria count is above $10^8$ CFU/mL, the preparation of the fermentation liquid is completed.

TABLE 1

| Strain | BLAST | | | SepsiTest™ BLAST | | |
|---|---|---|---|---|---|---|
| | Bacillus strains | Accession | Identities | Bacillus strains | Accession | Identities |
| PMB05 | B. amyloliquefaciens | | | B. amyloliquefaciens | AB255669 | 99.20% |
| | BCBR 11266 | EF423605 | (99.0%) 972/982 | B. atrophaeus | AB021181 | 99.00% |
| | BCBR 12815 | EF423604 | (99.0%) 972/982 | B. vallismortis | AB021198 | 98.80% |
| | BCBR 14710 | EF423606 | (99.0%) 972/982 | B. subtilis | AJ276351 | 98.80% |
| | B. subtilis | | | | | |
| | BCBR 14718 | EF423597 | (98.8%) 970/982 | | | |
| | BCBR 10058 | DQ993674 | (98.7%) 969/982 | | | |
| | BCBR 17437 | EF423600 | (98.7%) 969/982 | | | |

TABLE 2

| Strain | Bacillus strains | BLAST Accession | Identities |
|---|---|---|---|
| PMB05 | B. amyloliquefaciens | | |
| | UCMB5113 | HG328254 | (98.5%) 992/1007 |
| | FZB42 | CP000560 | (98.0%) 987/1007 |
| | UCMB5033 | HG328253 | (98.0%) 987/1007 |
| | B. subtilis | | |
| | Bs-916 | CP009611 | (98.0%) 987/1007 |
| | ATCC 19217 | CP009749 | (97.5%) 982/1007 |
| | ATCC 13952 | CP009748 | (95.0%) 957/1007 |

EXAMPLES

The examples below are used for illustrating the objectives and effects of the present invention, which are not to be seen as limiting.

Example 1: Dual Cultural Test Against Fungal Pathogens

The fungal pathogens used in this embodiment are strawberry anthracnose fungi (*C. gloeosporioides*). Add NA culture medium into the plate, and place 1 cm glass rings on the four corners at a distance of 2 cm from the center, and then add PDA culture medium to the plate as dual culture medium. First, incubate strain SC01 of strawberry anthracnose fungi (*C. gloeosporioides*) on a PDA plate. After five days, use a puncher with a diameter of 0.8 cm to cut out the mycelium at margin of colony, and place the cut-out piece at the center of the dual culture medium. Incubate antagonistic bacteria PMB05 in NB liquid culture medium, and incubate the culture until concentration reach 0.3 at OD600 value. Then draw 20 μl of culture and dispense it into the glass rings. Incubate the plate at the growth chamber under 28° C. and observe the results after 3 days. Repeat the process for 5 times. The inhibitory rate is calculated as follows:

$$\text{Inhibitory rate (\%)} = \frac{\left(\begin{array}{c}\text{hyphal length of control group} - \\ \text{hyphal length of experimental group}\end{array}\right)}{\text{hyphal length of control group}} \times 100$$

Figure 2:
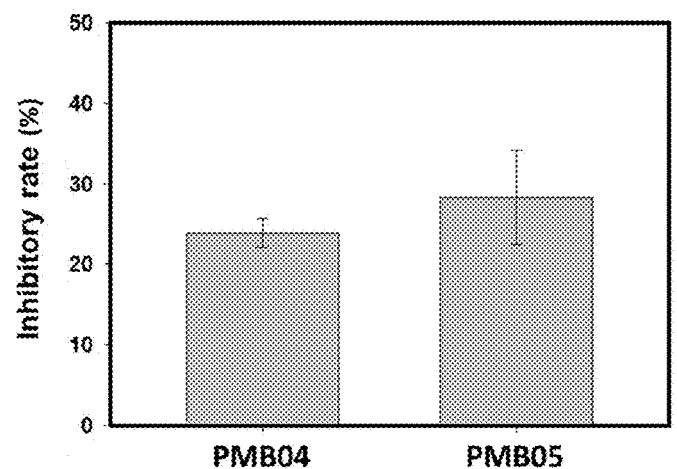
FIG. 2 is a graph illustrating the inhibitory rate in dual cultural test result of strain PMB05 against strawberry anthracnose.

The results are shown in FIG. 1 and FIG. 2. After 3 days of incubation, strain PMB05 (labelled as PMB05 in figures) can inhibit strain SC01 of strawberry anthracnose fungi (*C. gloeosporioides*) when compared to sterile H$_2$O in the control group (labelled as Blank). The inhibitory rates of PMB05 against strawberry anthracnose fungi (*C. gloeosporioides*) isolated strains SC01 IS 28.3%.

Example 2: The Effectiveness of Inhibiting Germ Tube Growth of Fungal Pathogens

This example is to analyse the effectiveness of strain PMB05 culture filtrate in inhibiting the hyphal length of fungal pathogen, and the fungal pathogens used are strawberry anthracnose fungi (*C. gloeosporioides*). First, the spores of anthracnose fungi (*C. gloeosporioides*) strain SC01 are washed down by sterile H$_2$O to prepare spore cell suspension of $10^5$ conidia/ml. Mix 100 μl of spore cell suspension with the nutrient source, 100 μl of 0.2% glucose solution, then add 100 μl of the aforementioned strain PMB05 culture filtrate in a microtube (the control group is added with sterile SYM liquid culture medium instead) and the total volume is accounted to 300 μl. The mixture is then put in a growth chamber at 25° C. After 12 hours, 50 μl of the mixture is drawn and dispensed into a cavity slide. Observe the slide by a microscope and count the number of budding spores in the slide. Repeat 3 times for each test and a total of 3 tests are performed.

Figure 3:
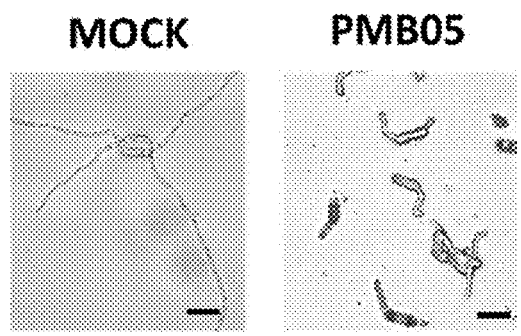
FIG. 3 shows the result of strain PMB05 inhibitory effect on strawberry anthracnose germ tube growth.
Figure 4:
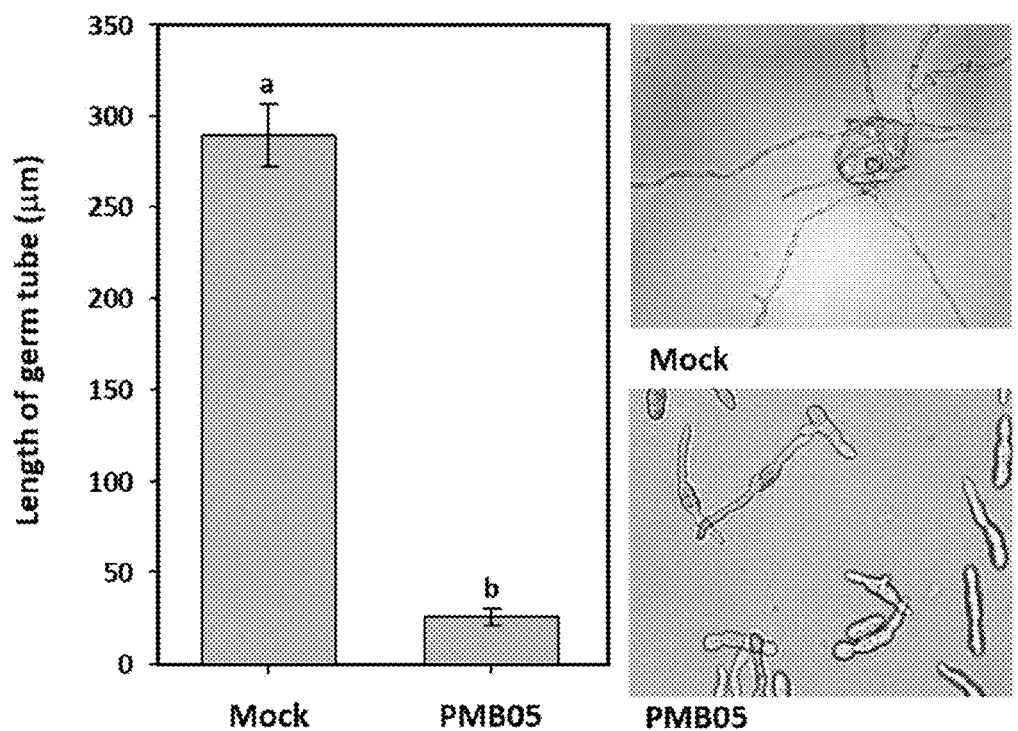
FIG. 4 is the graph illustrating the result of germ tube growth of strawberry anthracnose fungi after treated with strain PMB05.

The results are illustrated in FIG. 3 and FIG. 4, the germinated hyphal length in PMB05 treated group is 25.20 μm, which is significantly lower than the 266.88 μm germ tube length of untreated control group (labelled as Mock in figures). Furthermore, PMB05 filtrate has caused the swelling and deformity of some hyphal germ tubes.

Example 3: The Control Efficacies Against Fungal Pathogens on Plant Fruits

This example is to investigate the control efficacies of strain cell suspension against fungal pathogens on plant fruits, and the fungal pathogens used are strawberry anthracnose fungi. First, rinse the strawberry with tap water, disinfect the strawberry by soaking it into 1% sodium hypochlorite for 20 minutes, rinse it with sterile H$_2$O for 5 times and dry the strawberry. Next, prepare strain PMB05 cell suspension at OD600 value approx. 0.3 with sterile H$_2$O, submerge the disinfected strawberry fruit into this strain cell suspension, and dry the fruit for around 1 hour. Then, prepare spore cell suspension of strawberry anthracnose fungi strain SC01 at a concentration of $5 \times 10^5$ conidia/ml, drip 10 μl of spore cell suspension onto the strawberry fruit evenly, while the strawberry in control group is treated with water instead. After the fruit is incubated in the dark for 48 hours, put the fruit in the growth chamber and record the disease severity index after 3 days, and calculate the disease severity. Repeat the process with 6 strawberries in each test and perform three tests in total.

Figure 5:
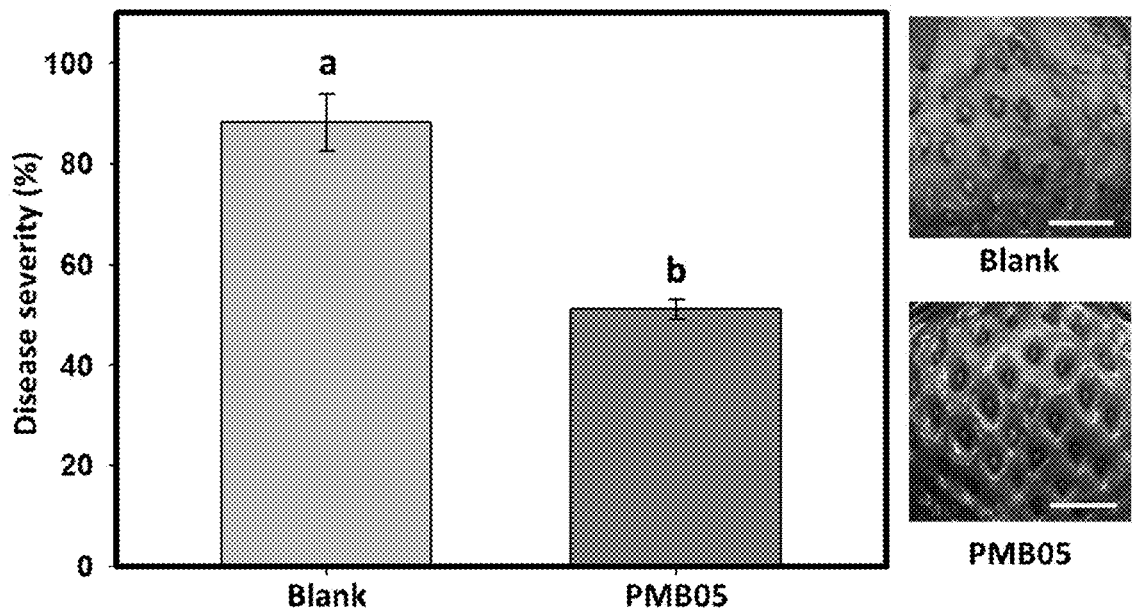
FIG. 5 shows the control efficacies of strain PMB05 against anthracnose fungi on strawberry fruits.

The result is illustrated in FIG. 5, the disease severity against strawberry anthracnose fungi after the treatment of strain PMB05 culture is 51.11%, which is significantly lower than that of 88.15% in the control group treated with water (labelled as Blank), and there are no obvious symptoms on the fruits.

Example 4: The Control Efficacies Against Fungal Pathogens on Pathogen-Free Seedlings and Commercial Seedlings This example is to investigate the control efficacies of strain PMB05 cell suspension against fungal pathogens on pathogen-free seedlings and commercial seedlings, and the fungal pathogens used are strawberry anthracnose fungi. First, prepare strain PMB05 cell suspension at OD600 value approx. 0.3 with sterile H$_2$O, evenly spray 3 ml of cell suspension onto pathogen-free strawberry seedlings and commercial strawberry seedlings, and wait for dry (approximately 1 hour). Next, prepare spore cell suspension of strawberry anthracnose fungi strain SC01 at a concentration of $10^5$ conidia/ml and evenly spray 1.5 ml of spore cell suspension onto strawberry plants, while the strawberry in control group is treated with water instead. After the plants are cultured in the dark for 48 hours, put them in the growth chamber and record the disease severity index in the first, second and fourth week for calculation of disease severity. Repeat the process with 4 strawberry plants in each test and perform three tests in total.

Figure 6:
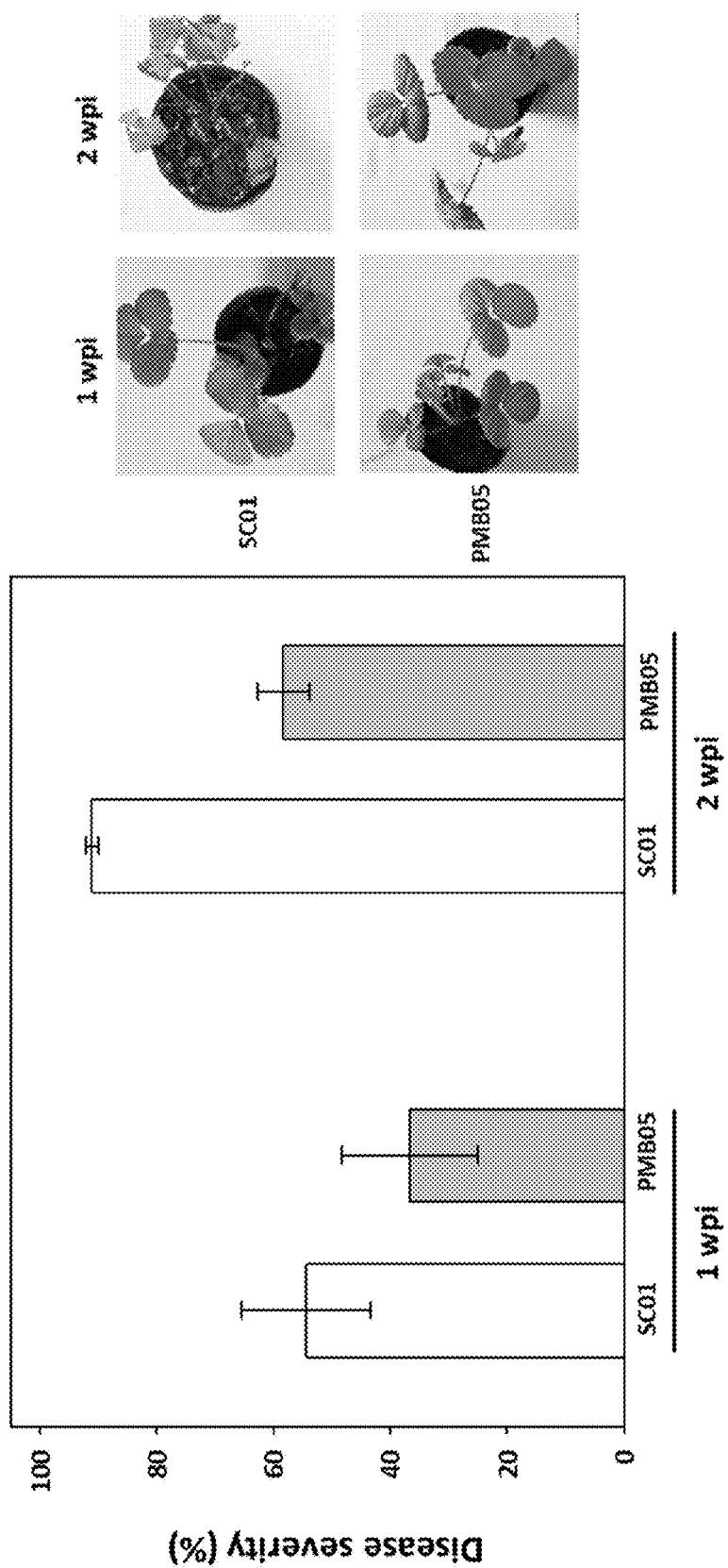
FIG. 6 shows the control efficacies of strain PMB05 against anthracnose fungi on pathogen-free seedlings of strawberry.

The results of disease control in pathogen-free strawberry seedlings are illustrated in FIG. 6. The disease severity of the strain PMB05 cell suspension-treated group is lower than that of the control group (labelled as SC01) after one week or two weeks. Wherein the disease control efficacy is more significant in two weeks after treatment, the disease severity decreases from 91.1% of the control group only inoculated with SC01 to 58.3%, and the disease control rate is 36.0%.

Figure 7:
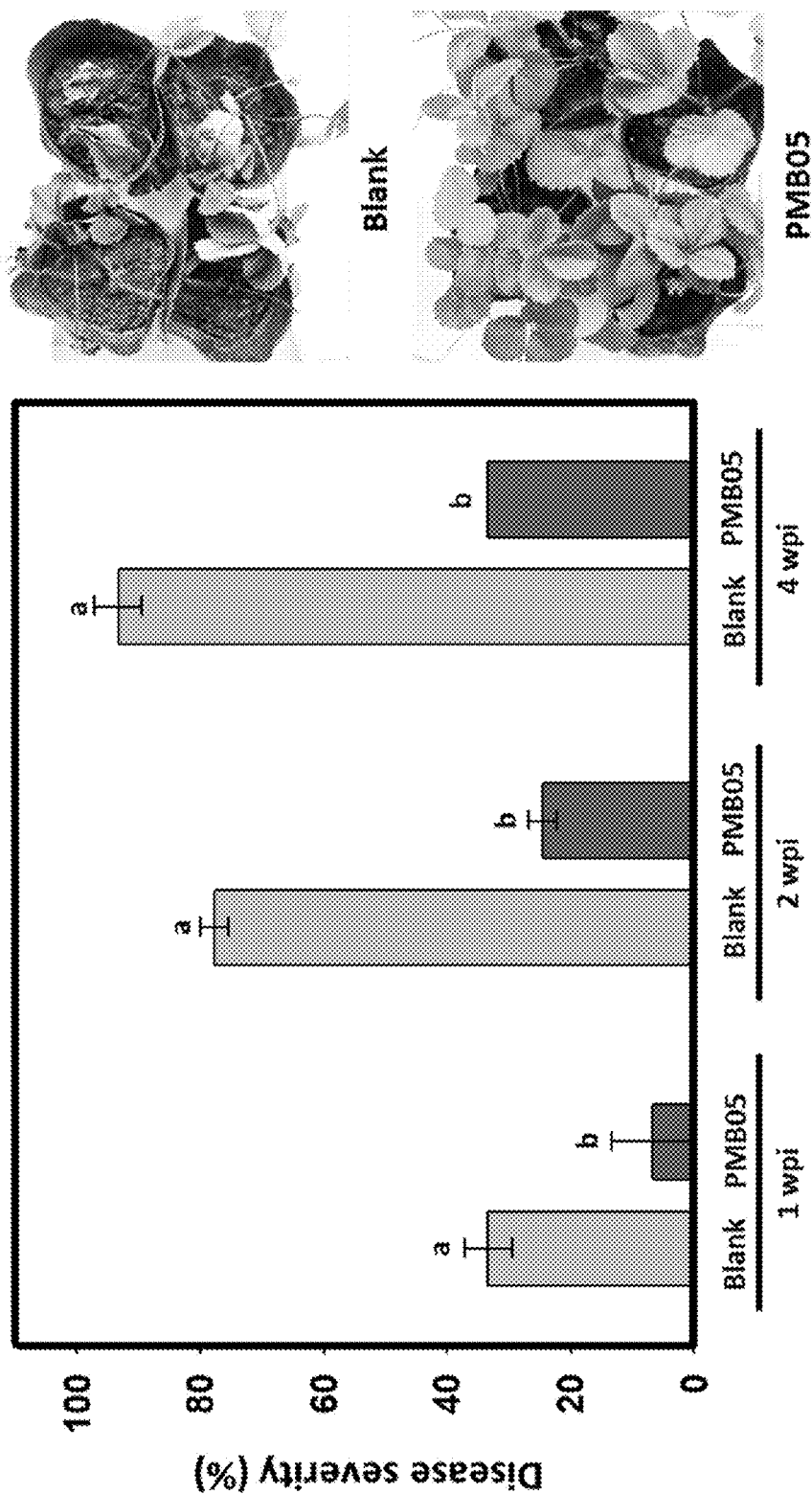
FIG. 7 shows the control efficacies of strain PMB05 against anthracnose fungi on commercial seedlings of strawberry.

The results of disease control in commercial strawberry seedlings are illustrated in FIG. 7. The disease severity of strain PMB05 cell suspension-treated group has no significant difference compare to that of the control group (labelled as Blank) after one week. However, after two weeks of the treatment, the disease severity of the strain PMB05 cell suspension-treated group is 24.4%, which is significantly lower than 77.8% of the control group. After four weeks, the efficacy against the disease can still be maintained (shown in FIG. 7 photo). Compared to the control group, the disease severity decreases from 93.3% to 33.3%, and the disease control rate is 64.3%.

Example 5: ROS Deposition Intensification after the Detection of Fungal Pathogens This example is to investigate the intensification by PMB05 treatment in the immune response of ROS deposition after detection of fungal pathogens by plant cells, and the fungal pathogens used are strawberry anthracnose fungi. To detect rapid production of $H_2O_2$, draw up 10 μl of water, strain culture filtrate and strain cell suspension with micropipettes respectively, discharge the liquid to strawberry leaf respectively, and wait for dry. Next, drip 10 μl of water and $10^5$ conidia/ml of strawberry anthracnose fungi strain SC01 onto the strawberry leaves treated in above steps respectively, and cut off the leaves after 0.5 hour. Cut the treated leaves into 0.3×1.0 cm strips, and remove the chlorophyll by 50% ethanol washing. Then, immerse them in PBS buffer (NaCl 8 g, KCl 0.2 g, $Na_2HPO_4$ 1.44 g, $KH_2PO_4$ 2.4 g in 1 L $H_2O$, pH 7.4) with the 20 μM final concentration solution of $H_2DCFDA$ (2',7'-dichlorodihydrofluorescein diacetate) (Molecular Probes, USA), and stain for 20 minutes, avoiding light and all are processed under exhaust treatment. After that, rinse the sample twice with PBS buffer and observe under a fluorescence microscope (Leics, Germany) with Excitation/Emission (465-495 nm/515-555 nm). The green fluorescence emission indicates the production of $H_2O_2$. The fluorescence microscopy images obtained above are quantitative analysed using the bioimaging software ImageJ. First, select the images needed for analysis and convert them to 8-bit grayscale. Then define the threshold values of fluorescence by adjusting "Adjust" and "Threshold" in "Image" option to obtain the quantitative data. Among the quantitative fluorescence data, the strawberry leaf only treated with water is set as 1, whereas the data of leaves under other treatments are divided by the data of control group. As a result, the quantification of relative fluorescence intensity ratio is obtained.

Figure 8:
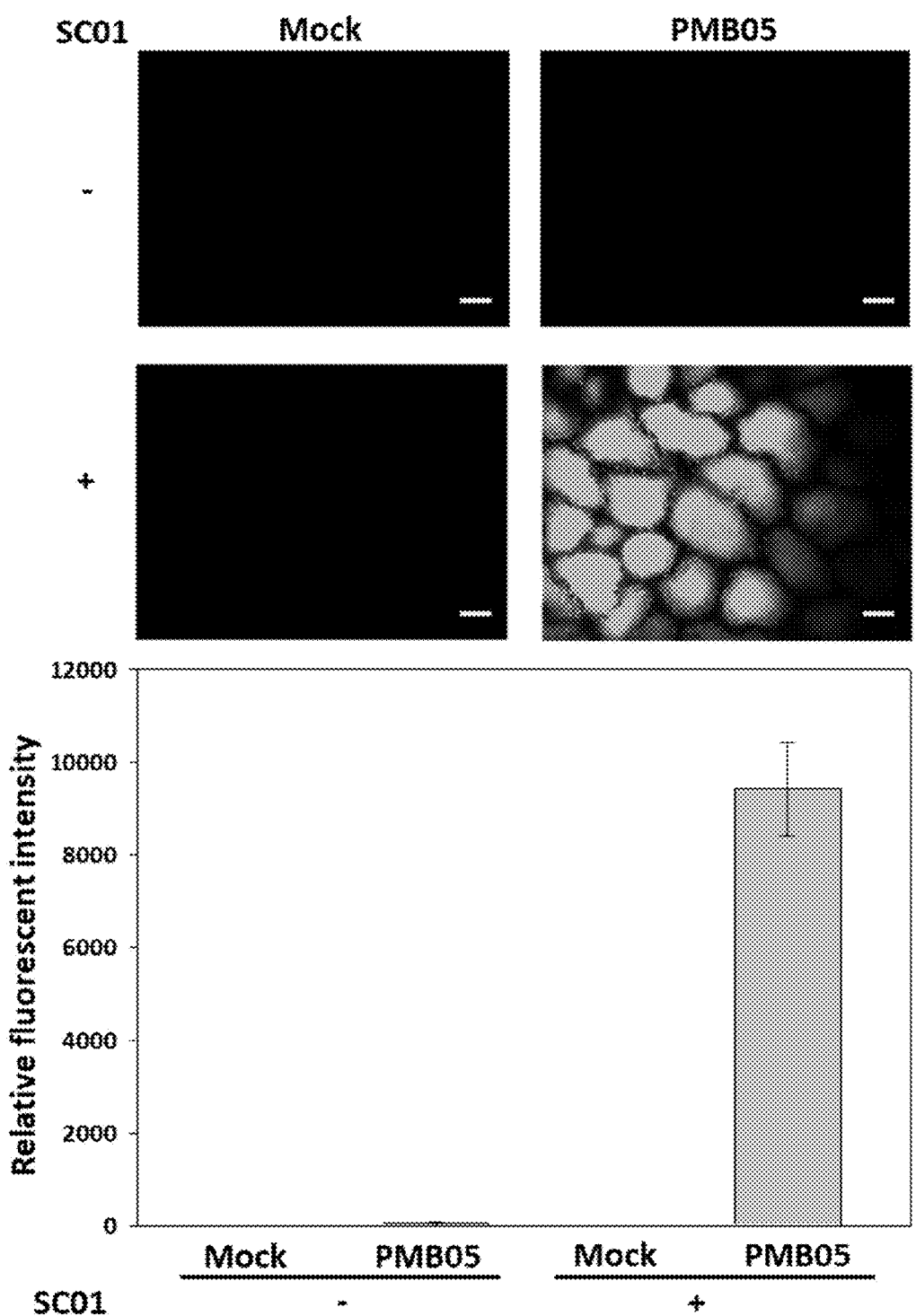
FIG. 8 shows the deposition of ROS intensified by strain PMB05 culture filtrate after the inoculation of anthracnose fungi in strawberry.

The experimental group results of leaves treated with strain culture filtrate are shown in FIG. 8, whereas the control group is treated with water (labelled as MOCK, SC01−). In the production of ROS, the leaves only treated with anthracnose fungi (labelled as MOCK, SC01+), have relative fluorescence intensity of merely 10 times; for the leaves only treated with strain PMB05 culture filtrate (labelled as PMB05, SC01−), the strawberry leave cells have relative fluorescence intensity of merely 45 times. However, for the leaves treated with both strain PMB05 culture filtrate and anthracnose fungi, the relative fluorescence intensity ratio of $H_2O_2$ of strawberry leaf cells reach up to 9,414 times.

Figure 9:
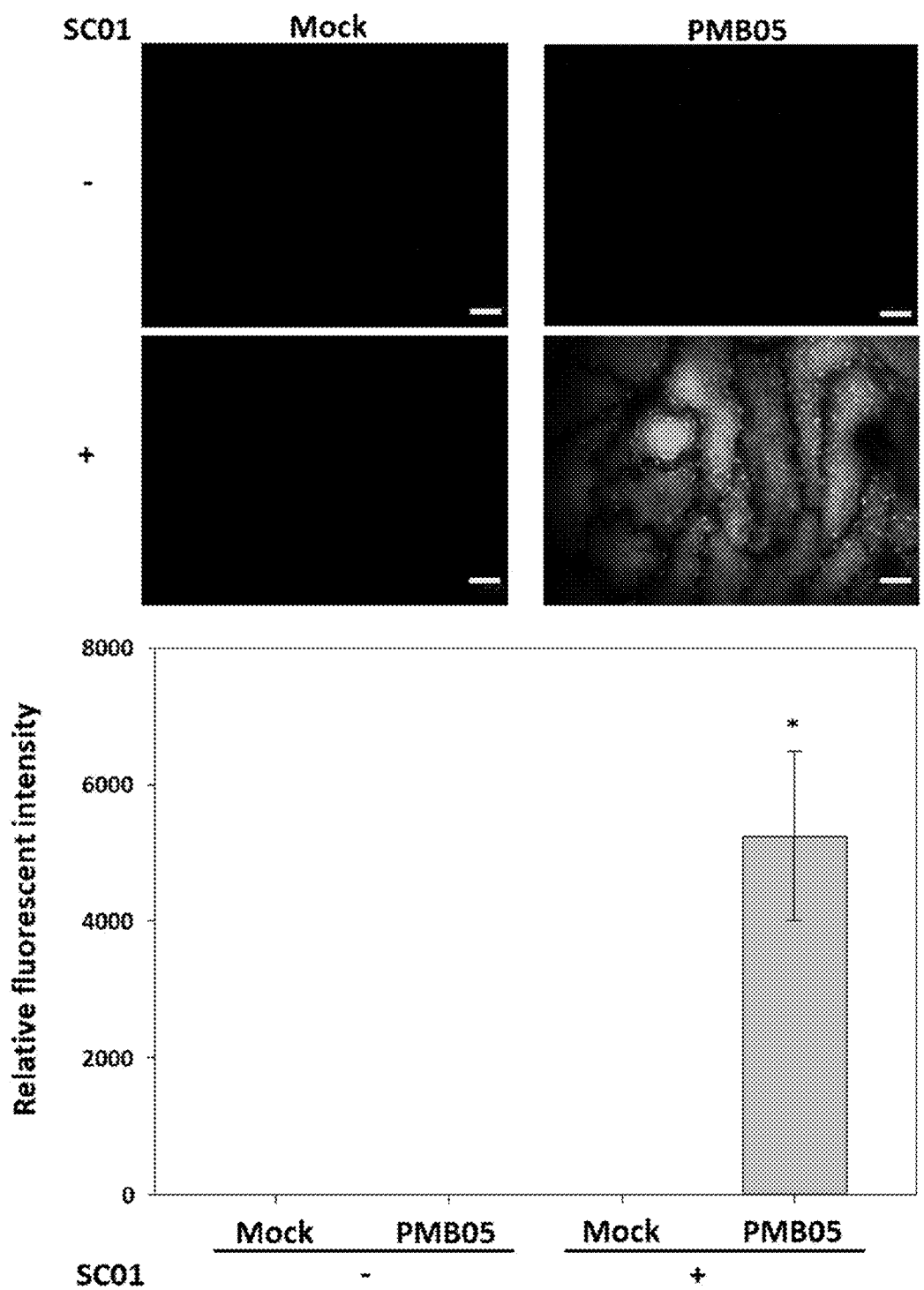
FIG. 9 shows the deposition of ROS intensified by strain PMB05 cell suspension after the inoculation of anthracnose fungi in strawberry.

Furthermore, the leaves are treated with strain PMB05 cell suspension in order to determine whether the living cells of strain PMB05 have the ability to strengthen the production of $H_2O_2$ after detection of fungal pathogens. The results are shown in FIG. 9, after strain PMB05 cell suspension-treated strawberry leaf cells are inoculated with anthracnose fungi, the relative fluorescence intensity is 5247 times, which is significantly higher than that of the control group (labelled as MOCK, SC01−).

Example 6: Callose Deposition Intensification after the Detection of Fungal Pathogens This example is to investigate the intensification by PMB05 treatment in immune response of callose deposition after detection of fungal pathogens by plant cells, wherein the fungal pathogens used are strawberry anthracnose fungus. First, draw up 10 μl of water, strain culture filtrate and strain cell suspension with micropipettes respectively, discharge the liquid to strawberry leaf respectively, and wait for dry. Next, drip 10 μl of water and $10^5$ conidia/ml of strawberry anthracnose fungi strain SC01 onto the strawberry leaves treated in said steps respectively, and cut off the leaves after 24 hours. Cut the treated leaves into small strips and decolorize the leaf strips for 24 hours with 95% ethanol. Then, immerse the leaves in 0.1 M PB buffer (1 M $Na_2HPO_4$ 93.2 ml, 1 M $NaH_2PO_4$ 6.8 ml in 1 L $H_2O$, pH8.0) that contains 0.01% aniline blue. After 2 hours, observe the leaves under a fluorescence microscope (Leica, Germany) with Excitation/Emission (465-495 nm/515-555 nm wavelength). The blue fluorescence emission indicates the deposition of callose. The fluorescence microscopy images obtained above are quantitative analysed using the bioimaging software ImageJ. First, select the images needed for analysis and convert them to 8-bit grayscale. Then define the threshold values of fluorescence by adjusting "Adjust" and "Threshold" in "Image" option to obtain the quantitative data. The calculation of quantification of relative fluorescence intensity ratio of this embodiment is similar to that in Embodiment 5.

Figure 10:
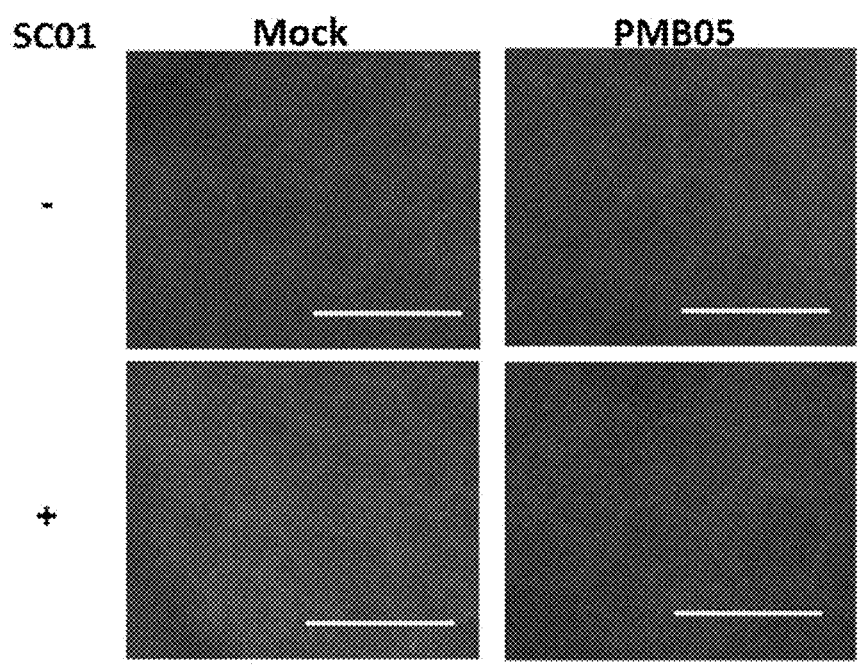
FIG. 10 shows the deposition of callose intensified by strain PMB05 culture filtrate after the inoculation of anthracnose fungi in strawberry.
Figure 11:
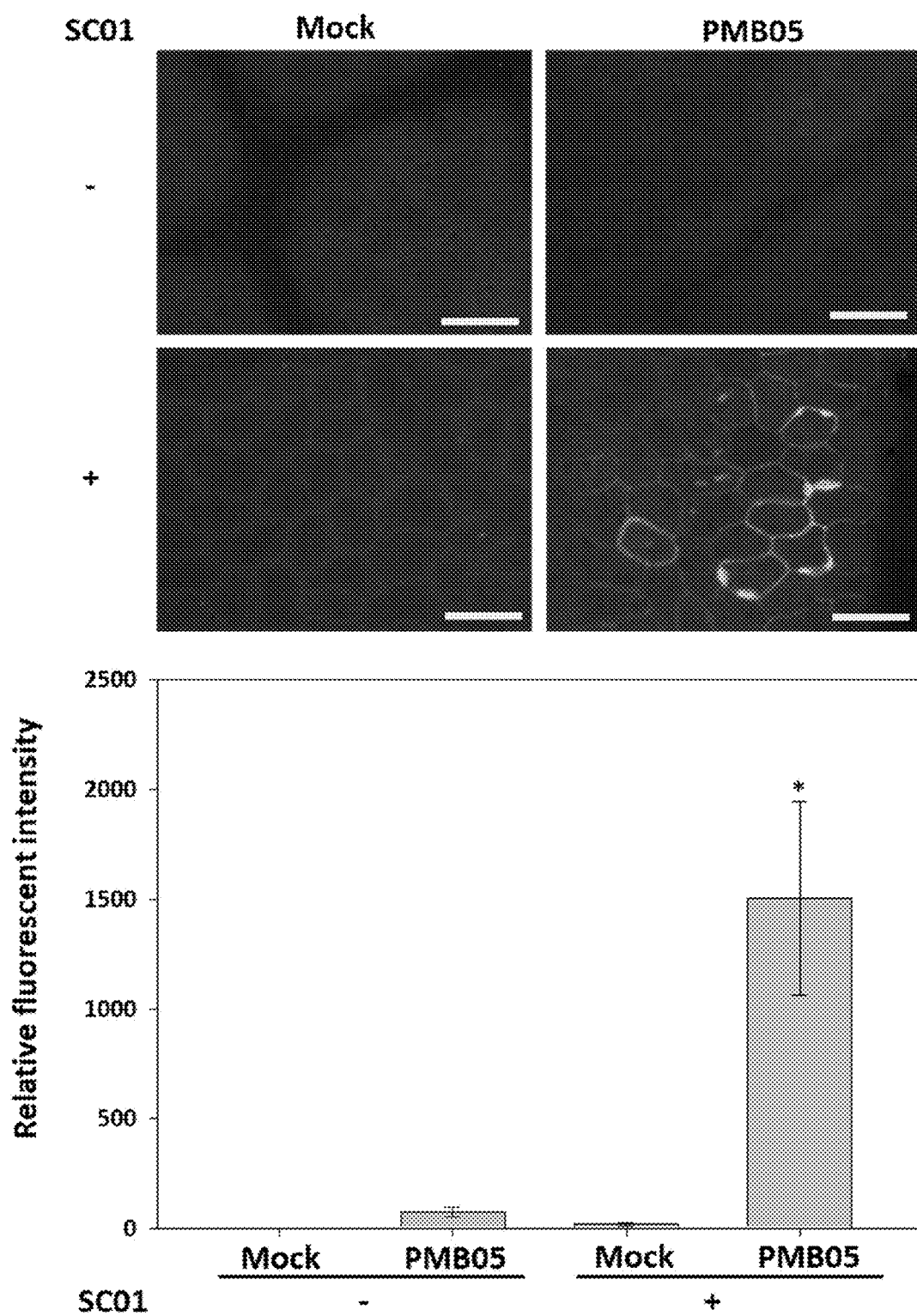
FIG. 11 shows the deposition of callose intensified by strain PMB05 cell suspension after the inoculation of anthracnose fungi in strawberry.
Figure 12:
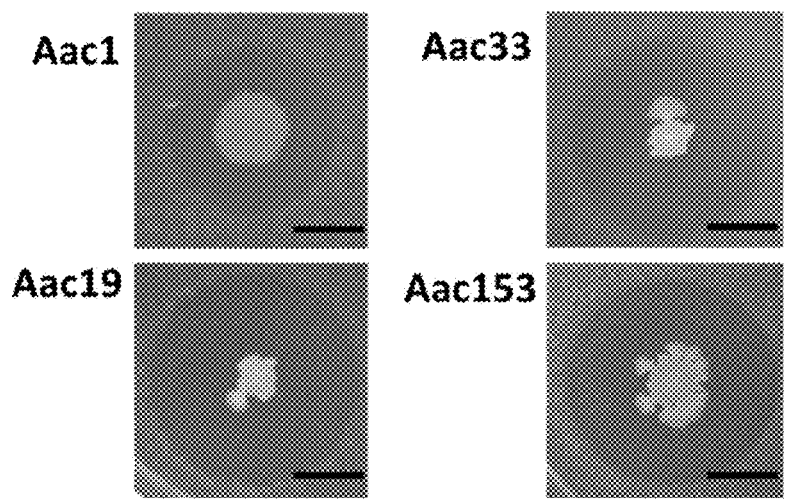
FIG. 12 shows the result of dual cultural test of strain PMB05 against bacterial fruit blotch.
Figure 13:
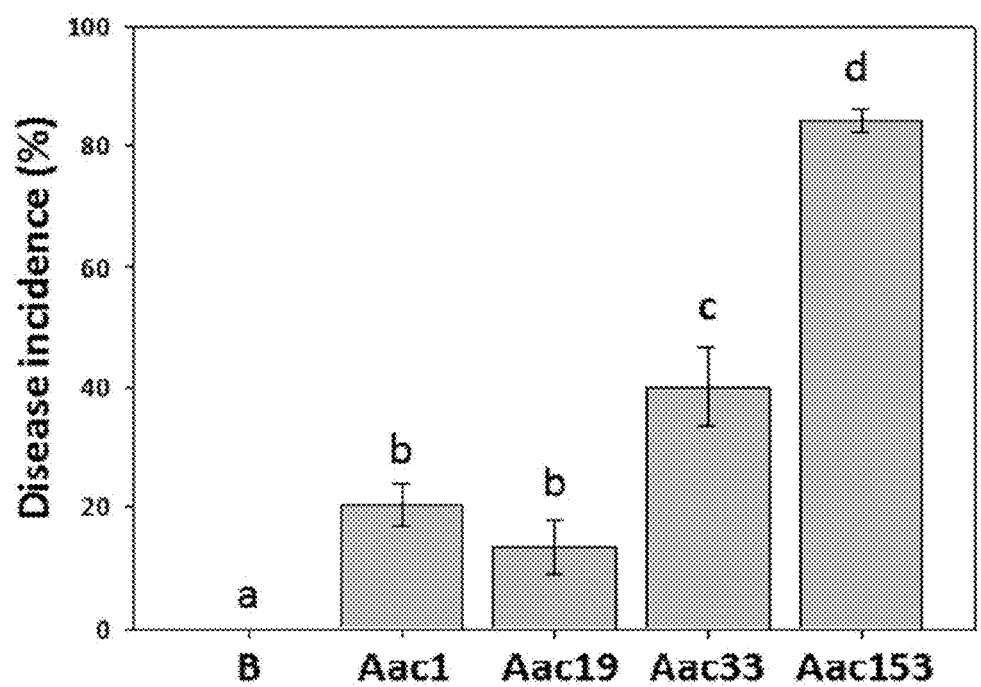
FIG. 13 shows the incidence of bacterial fruit blotch inoculated with different *Acidovorax citrulli* strains on watermelon seeds.
Figure 14:
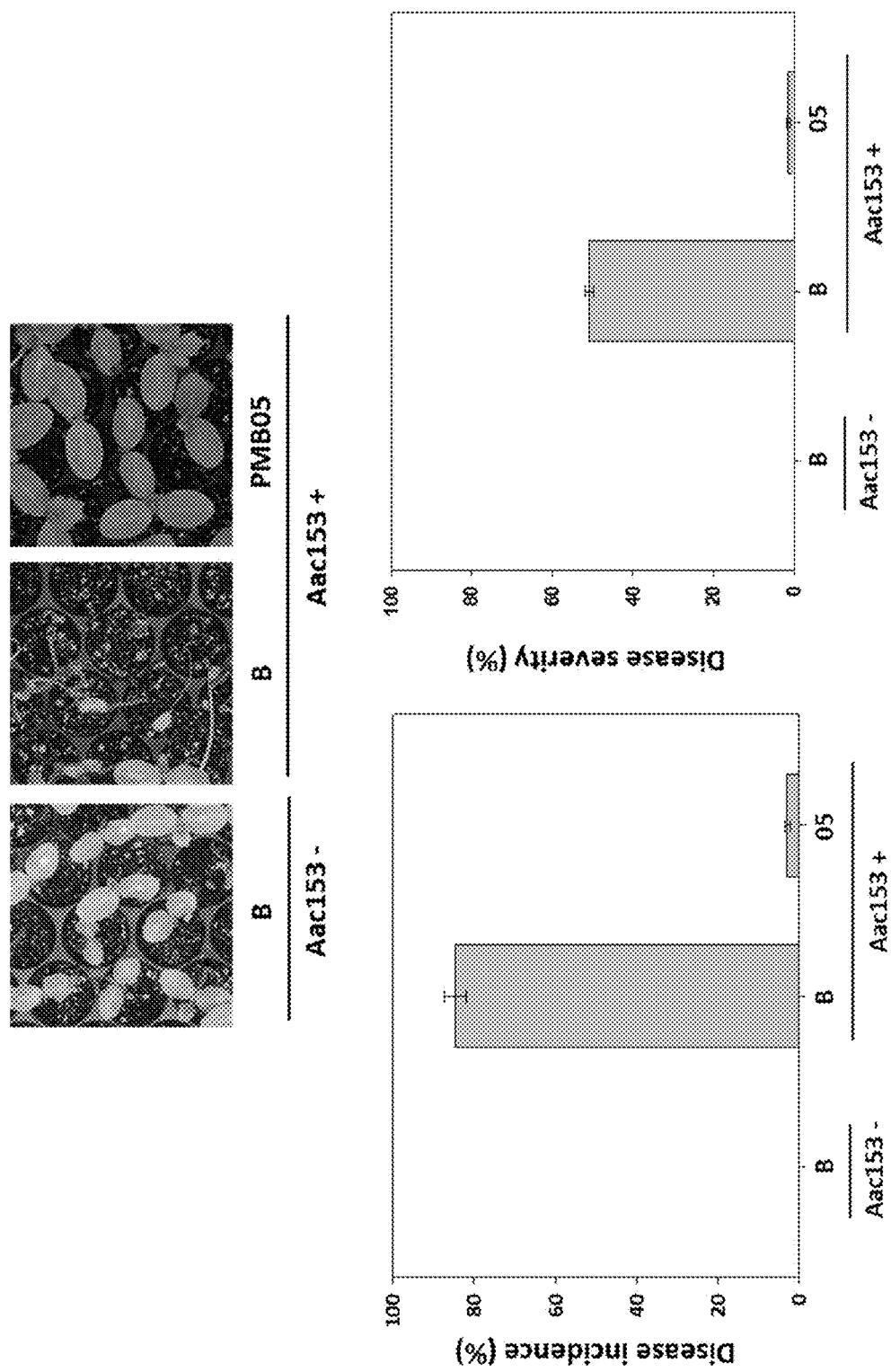
FIG. 14 shows the control efficacies of strain PMB05 cell suspension against bacterial fruit blotch on watermelon seeds.
Figure 15:
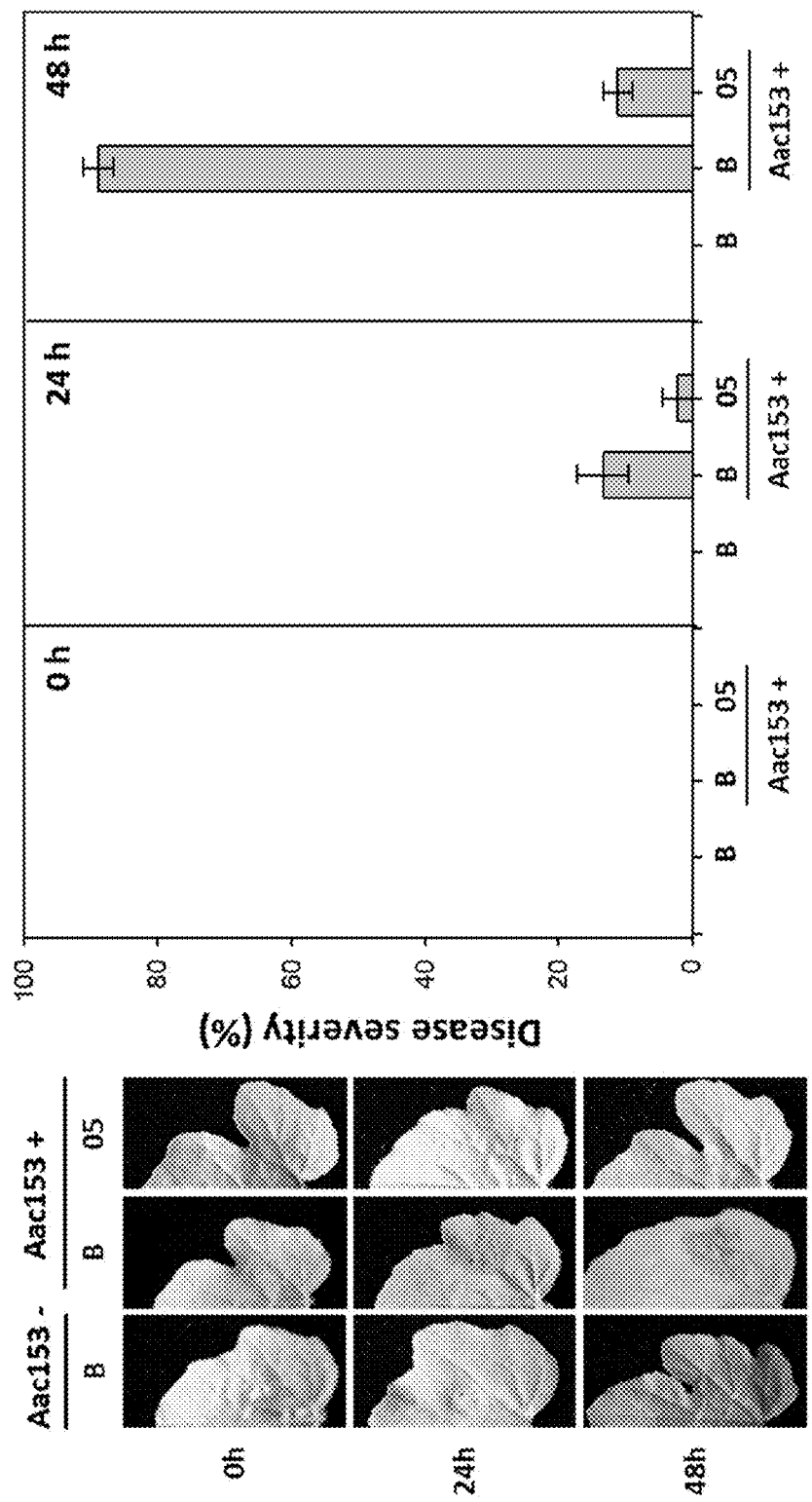
FIG. 15 shows the control efficacies of strain PMB05 cell suspension against bacterial fruit blotch on watermelon leaves.

The experimental group results of leaves treated with strain culture filtrate are shown in FIG. 10. Leaves only treated with strain PMB05 culture filtrate or treated with both filtrate and anthracnose fungi cannot activate the deposition of callose by strawberry leaves. However, as in the results shown in FIG. 11, if strain PMB05 cell suspension that contains living cells is used and with both the treatment of strain PMB05 cell suspension and anthracnose fungi, the deposition of callose on surrounding cells of strawberry leaves increases. Compared to the control group which is only treated with water, the relative fluorescence intensity of strawberry leaf cells increases to 1,504 times.

Example 7: Dual Cultural Test of Bacterial Pathogens

In one example, the bacterial pathogens are bacteria of bacterial fruit blotch (*Acidovorax citrulli*). First, use the inoculation needle to dip the strain PMB05 colony that has been incubated in the NA solid culture medium for 24 hours. The bacteria are then transferred to the NA solid culture medium by a single stab, and incubate the culture medium in an incubator at 28° C. for 16-18 hours. Next, to prepare bacterial cell suspension at OD600 value 0.3, use bacterial fruit blotch bacteria (*A. citrulli* strain Aac1, Aac19, Aac33 and Aac153) that have been incubated for 48 hours with sterile $H_2O$. The bacterial concentration will be approximately $10^8$ CFU/ml. After that, fill a glass spray bottle with the prepared bacterial cell suspension and evenly spray bacterial pathogens onto the foresaid NA solid culture medium that has cultured strain PMB05. After incubate the culture medium in an incubator at 28° C. for 48 hours, observe the formation of zone of inhibition and calculate the size of zone of inhibition. The formula for calculating zone of inhibition is as follows:

[Outer diameter of the clear zone (transparent circle) (mm)−Diameter of colony (mm)]/2=Zone of inhibition (mm)

Repeat the test for three times, and use Tukey-Kramer method ($p<0.05$) for statistically analyzing the data obtained from one of the repeated test.

The results are illustrated in FIG. 12. Strain PMB05 can inhibit the *Acidovorax citrulli* growth on plates, and can also inhibit different strains of *Acidovorax citrulli*. The zone of inhibition of strain PMB05 against strains of *Acidovorax citrulli* Aac1, Aac19, Aac33, Aac153 are 6.33±0.34 mm, 13.64±1.85 mm, 7.91±1.13 mm, 8.32±1.20 mm respectively.

Example 8: Control Efficacies Against Bacterial Pathogens in Seeds

In one example, the bacterial pathogens used are bacteria of bacterial fruit blotch (*Acidovorax citrulli*). First, treat the watermelon seeds with bacterial cell suspension of *A. citrulli* strains Aac1, Aac19, Aac33, Aac153 and analyze the occurrence of bacterial fruit blotch. The results are illustrated in FIG. 13, the disease severity of *A. citrulli* strains Aac1, Aac19, Aac33, Aac153 on watermelon are 20.4%, 13.5%, 40.1% and 84.1% respectively (the control group using sterile $H_2O$ is labelled as B). Due to higher disease severity of Aac153, the strain of *Acidovorax citrulli* used in the following tests and embodiments 9-14 is Aac153.

In order to access the disease control effect of strain PMB05 cell suspension to bacterial pathogens, *A. citrulli* Aac153 colonies that have been incubated for 48 hours are picked. The colonies are massively amplified in NA solid culture medium for 24 hours, *Acidovorax citrulli* cell suspension at OD600 value 0.3 is prepared with sterile $H_2O$ that contains 0.1% carboxymethyl cellulose (CMC) (Sigma, USA), and the bacterial concentration is approximately $10^7$ CFU/ml. Then soak the seeds in the bacterial cell suspension, and incubate them with shaking at 28° C., 200 rpm for 24 hours. Dry the seeds afterwards. After drying the seeds, soak them in strain PMB05 cell suspension at OD600 value 0.3, in which the bacterial concentration is approximately $10^7$ CFU/ml. Incubate them with shaking under the same condition for 24 hours to finish the treatment of seeds. For the control group, after the treatment of bacterial fruit blotch, treat the seeds with sterile 0.1% CMC solution. After drying the treated seeds from the above process, plant them in plug trays of diameter 4.5 cm and place the trays in greenhouse. Analyze the disease incidence and disease severity at the $21^{st}$ day after sowing.

Disease incidence shows the plant infection of bacterial fruit blotch, which is expressed as a percentage, and 50 plants are assessed in each test and 3 repeat tests are performed. Disease severity is the degree of bacterial fruit blotch occurrence in watermelon, and is recorded using the following 3-level scale: (level 0: no symptoms; level 1: syndromes of water soaked lesions on cotyledons; level 2: necrosis symptoms on true leaves; level 3: wilting and death of the plant). Count the number of plants in each level; 50 plants are assessed in each test and 3 repeat tests are performed. Finally, convert the data to disease severity and the formula is as follows:

$$\text{Disease Severity (\%)}=[(0\times N_0+1\times N_1+2\times N_2+3\times N_3)/(3\times 50)]\times 100\%$$

Similarly, use Tukey-Kramer method ($p<0.05$) for statistically analyzing the data obtained from one of the repeat test.

The results are illustrated in FIG. 14. The occurrence of bacterial fruit blotch is lower in experiment group treated with strain PMB05 when compared to the control group only inoculated with Aac153. In the control group only inoculated with Aac153, the disease incidence and disease severity are 84.6% and 50.9% respectively. In the experiment group treated with PMB05, the disease incidence and disease severity are 2.9% and 1.4% respectively, which are significantly different from the results in the control group.

Example 9: Control Efficacies Against Bacterial Pathogens on Leaves

This example is to access the disease control effect of strain PMB05 cell suspension to bacterial fruit blotch on plant leaves. Before inoculation of bacterial fruit blotch, strain Aac153 is acclimated by the antibiotic, rifampicin, and then a strain Aac153$^r$ that has a similar growth rate to that of the wild strain is obtained. Next, prepare Aac153$^r$ bacterial cell suspension, and mix Aac153$^r$ cell suspension with strain PMB05 cell suspension (both at 0.3 OD600 value respectively) in the volume ratio of 1:1 to acquire a mixed bacterial cell suspension. The mixed bacterial cell suspension is inoculated to watermelon leaves planted for 21 days by injection; observe the disease symptoms after 0, 24 and 48 hours respectively. Also, calculate the disease severity of Aac153$^r$ and bacterial population of *Acidovorax citrulli* (CFU/g leaf) at the same time. Degree of bacterial fruit blotch occurrence on watermelon leaves is recorded using the following 3-level scale: (level 0: no symptoms; level 1: symptoms of water soaked lesions in the inoculated area; level 2: symptoms of yellow to brown spots in the inoculated area; level 3: all the inoculated areas are black brown necrotic spots). Count the number of leaves in each level, whereas 5 leaves are assessed in each test and 3 repeat tests are performed. Finally, convert the data to disease severity and the formula is as follows:

$$\text{Disease Severity (\%)}=[(0\times N_0+1\times N_1+2\times N_2+3\times N_3)/(3\times 5)]\times 100\%$$

For the bacterial population analysis of *Acidovorax citrulli*, take 0.1 g of leaf and homogenize the leaf. Then perform serial dilution by adding sterile $H_2O$, incubate the bacteria in NA solid culture medium which contains 100 ppm of rifampicin, at 28° C. for 48 hours, and then calculate the colonies. Each test accesses 5 leaves and 3 repeat tests are performed. In reproducibility conditions, use Tukey-Kramer method ($p<0.05$) for statistically analyzing the data obtained from one of the repeat test.

The results of symptoms observation and disease severity are illustrated in FIG. 15. In the group only inoculated with Aac153$^r$, typical necrosis symptoms of black brown spots are observed on leaves after 48 hours from inoculation. Whereas in the group inoculated with both Aac153$^r$ and PMB05, there are only small water soaked lesions on leaves, or no symptom is observed. The results of disease severity shown that after 24 hours from inoculation, the disease severity of the group only inoculated with Aac153$^r$ rises to 13.3%, and the disease severity of the group inoculated with both Aac153$^r$ and PMB05 is 2.2%; 48 hours after inoculation, the disease severity of the group only inoculated with Aac153$^r$ increases to 88.9%, whereas that of the PMB05 experimental group is significantly lower, and its disease severity is 11.1%.

Figure 16:
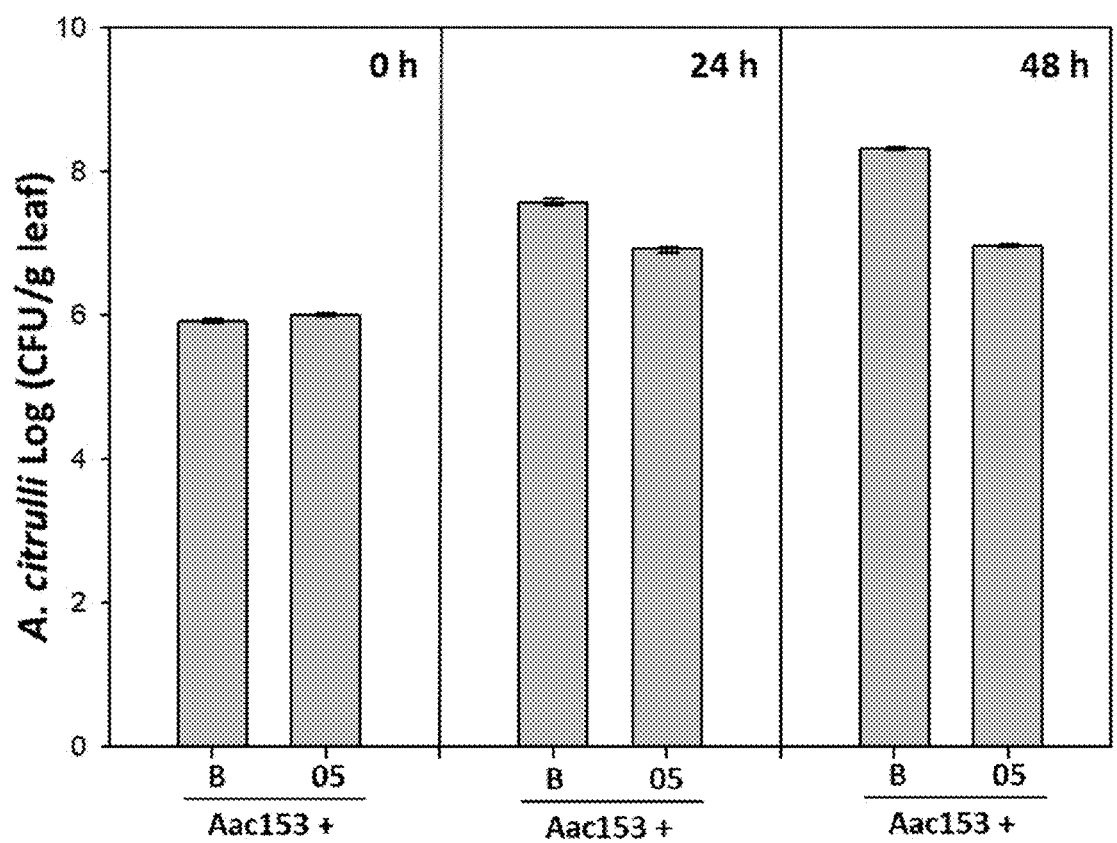
FIG. 16 shows the dynamic of *Acidovorax citrulli* population in plant leaves inoculated with strain PMB05.

Furthermore, the analysis of bacterial population dynamics of Aac153$^r$ is shown in FIG. 16. At 0 hour after inoculation, the original bacterial population for Aac153$^r$ of the control group and experimental group are approximately $8.3 \times 10^5$ CFU/g leaf. At 24 hours after inoculation, the bacterial population of experimental group PMB05 is $8.2 \times 10^6$ CFU/g leaf, which is lower than that of the control group only treated with Aac153$^r$. The bacterial population of control group only treated with Aac153$^r$ (labelled as B) after 24 hours from inoculation is $3.8 \times 10^7$ CFU/g leaf. Further, at 48 hours after inoculation, the Aac153$^r$ population in experimental group PMB05 is $9.2 \times 10^6$ CFU/g leaf, the bacterial population is still lower than the population of control group only treated with Aac153$^r$, which is $2.0 \times 10^8$ CFU/g leaf.

Example 10: Control Efficacies Against Bacteria of Citrus Bacterial Canker

The current example is to evaluate the control efficacies against bacterial pathogens on lemon plants treated with strain PMB05 fermentation liquid, and the bacterial pathogens used are bacteria of citrus bacterial canker (*Xanthomonas citri* subsp. *citri*). The treatment method is to dilute the aforesaid fermentation liquid to 200× dilution, and spray the dilution on the lemon plants in the field. The treatment is given every two weeks, for a total of 3 treatments. Also in the investigation of disease, randomly select 5 branches from each lemon tree, examine the proportion of citrus bacterial canker occurrence in the leaves and fruit trees, and calculate disease index. Examine the plants every two weeks and each time examines 5 trees; the investigation is continued for 18 weeks.

Figure 22:
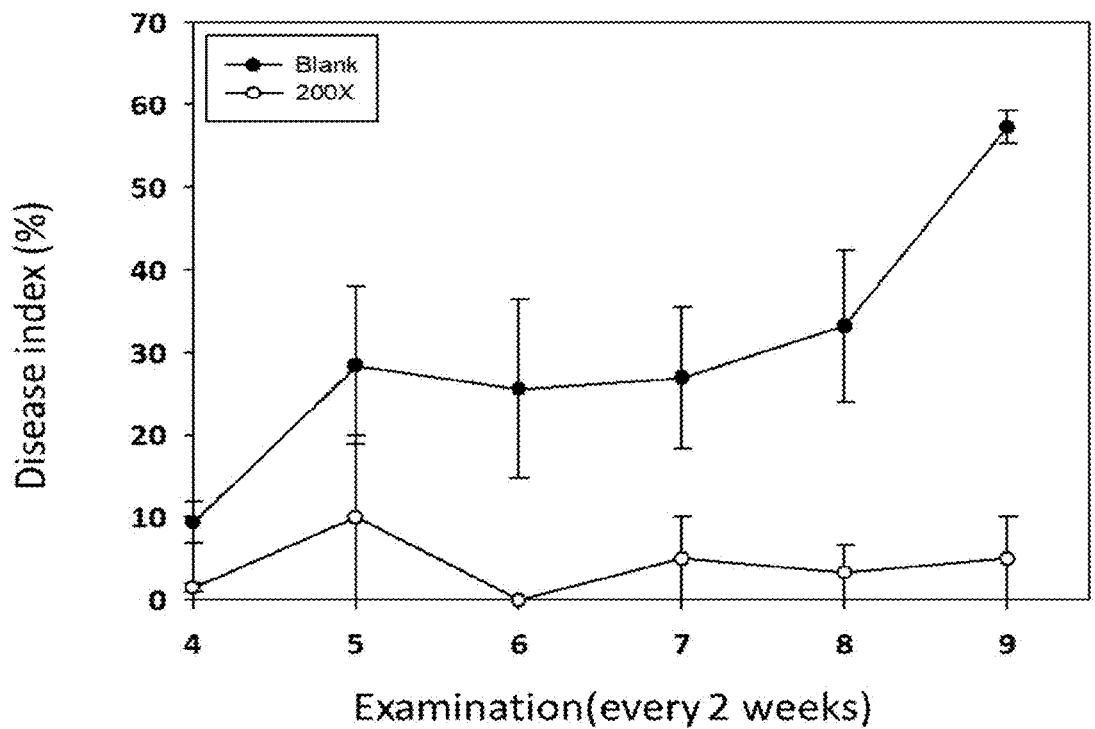
FIG. 22 shows the control efficacies of strain PMB05 against citrus bacterial canker on lemon fruits.
Figure 23:
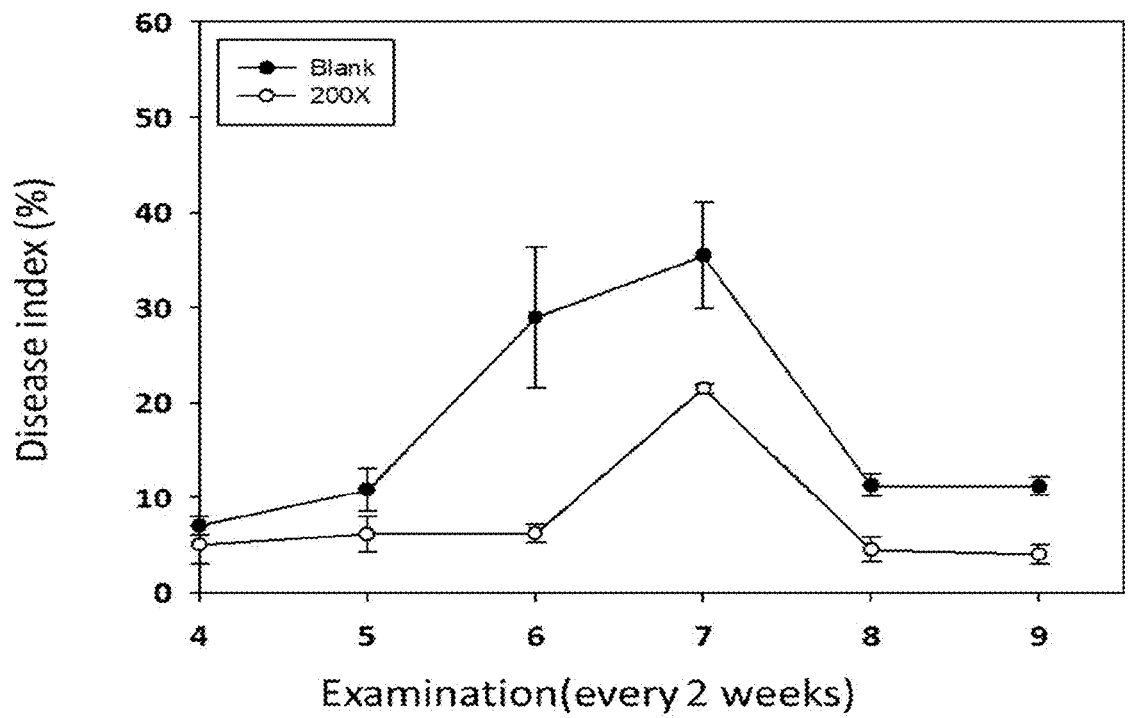
FIG. 23 shows the control efficacies of strain PMB05 against citrus bacterial canker on lemon leaves.
Figure 24:
FIG. 24 shows control efficacies of strain PMB05 revealed by symptoms of citrus bacterial canker.
Figure 24:

The results are shown in FIG. 22 and FIG. 23. After the plants are treated with strain PMB05 fermentation liquid, whether in the conditions of bacterial canker in leaves or fruits, the disease indexes in PMB05 fermentation liquid-treated group are lower than the control group that receives no treatment (labelled as Blank) after the 4$^{th}$ examination. Further shown in FIG. 24, obvious symptoms are observed in the untreated control group while no obvious symptoms are observed in the group of trees treated with the 200× dilution of strain PMB05 fermentation liquid.

Example 11: ROS Deposition Intensification after the Detection of the Bacterial Pathogen of Bacterial Fruit Blotch in Plant The current example is to investigate the intensification by PMB05 treatment in the immune response of ROS deposition after detection of bacterial pathogens in plant. First, mix *Acidovorax citrulli* strain Aac153 and strain PMB05 cell suspension of OD600 value 0.3 in the volume ratio of 1:1. The mixed bacterial cell suspension is inoculated to watermelon true leaves planted for 21 days by injection; 5 plants are inoculated in each process, leaves from 3 plants are collected randomly 1 hour after inoculation. After using a blade to cut the leaves into strips of length 0.4 cm and width 0.2 cm, remove the chlorophyll by 50% alcoholic washing. Rinse the leaf strips with PBS buffer (NaCl 8 g, KCl 0.2 g, Na$_2$HPO$_4$ 1.44 g, KH$_2$PO$_4$ 2.4 g in 1 L H$_2$O, pH 7.4). Dissolve H$_2$DCFDA (2',7'-dichlorodihydrofluorescein diacetate) (Molecular Probes, USA) into PBS buffer to obtain H$_2$DCFDA stain buffer (20 μM final concentration). Then immerse the leaf strips in H$_2$DCFDA stain buffer, perform vacuum air-extraction for 3 minutes and stain for 20 minutes, avoiding light. Rinse the stained leaf strips with PBS buffer twice. Finally, put the leaf strips under a fluorescence microscope (Leica, Germany) with Excitation/Emission (465-495 nm/515-555 nm) to observe the production of ROS. The images are extracted using software Leica application suite V4, and bioimaging software Image) is used to quantify and analyse the fluorescence intensity. Each test accesses 3 leaves and 3 repeat tests are performed, then use Tukey-Kramer method (p<0.05) for statistically analyzing the data obtained from one of the repeat test.

Figure 17:
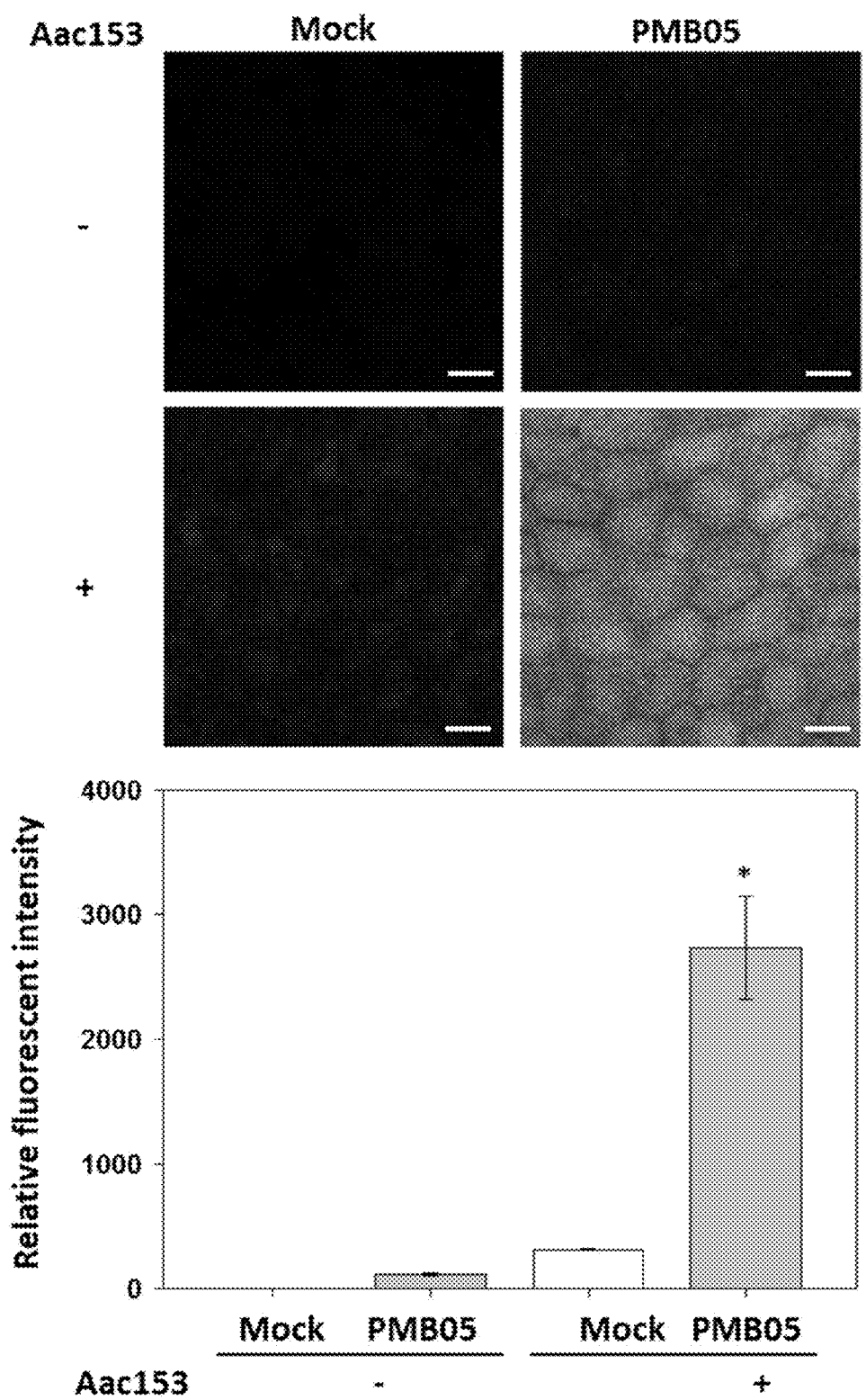
FIG. 17 shows the deposition of ROS intensified by strain PMB05 cell suspension after the inoculation of *Acidovorax citrulli* in watermelon.

The results are illustrated in FIG. 17. After 1 hour from the treatment, observe the group of leaves only treated with Aac153, under a fluorescence microscope, and there is a trace amount of H$_2$O$_2$ production; in the group treated with both Aac153 and PMB05, an increasing trend of H$_2$O$_2$ production is observed. Moreover, in the group only treated with PMB05, there is no H$_2$O$_2$ production. After quantification of the fluorescence signals of H$_2$O$_2$, set the control group only treated with water as the standard. The results demonstrate that the relative fluorescence intensity of control group solely treated with Aac153 is 313.7 times, the relative fluorescence intensity of control group solely treated with PMB05 is 112.3 times, and the relative fluorescence intensity of experimental group treated with both Aac153 and PMB05 is 2733.0 times. It shows that PMB05 can significantly intensify the rapid production of H$_2$O$_2$ which is induced by the watermelon's detection of *Acidovorax citrulli* strain Aac153.

Example 12: Callose Deposition Intensification after the Detection of the Bacterial Pathogens The current example is to investigate the intensification by PMB05 treatment in immune response of callose deposition after detection of bacterial pathogens. The inoculation by injection method is same as the previous embodiment 11. 5 plants are inoculated in each process; leaves from 3 plants are collected randomly 8 hours after inoculation. After using a blade to cut the leaves into strips of length 0.4 cm and width 0.2 cm, immerse the leaf strips in 95-100% alcohol for 24 hours to remove the chlorophyll. Next, immerse the leaf strips in 0.1 M PB buffer (1 M Na$_2$HPO$_4$ 93.2 ml, 1 M NaH$_2$PO$_4$ 6.8 ml in 1 L H$_2$O, pH8.0) that contains 0.01% aniline blue for 1 hour. Put the leaf strips under a fluorescence microscope of Excitation/Emission (wavelength 465-495 nm/515-555 nm) to observe the deposition of callose. The images are extracted using software Leica application suite V4, and bioimaging software ImageJ is used to quantify and analyse the fluorescence intensity. Each test accesses 3 leaves and 3 repeat tests are performed, then use t-test (p<0.05) for statistically analyzing the data obtained from one of the repeat test.

Figure 18:
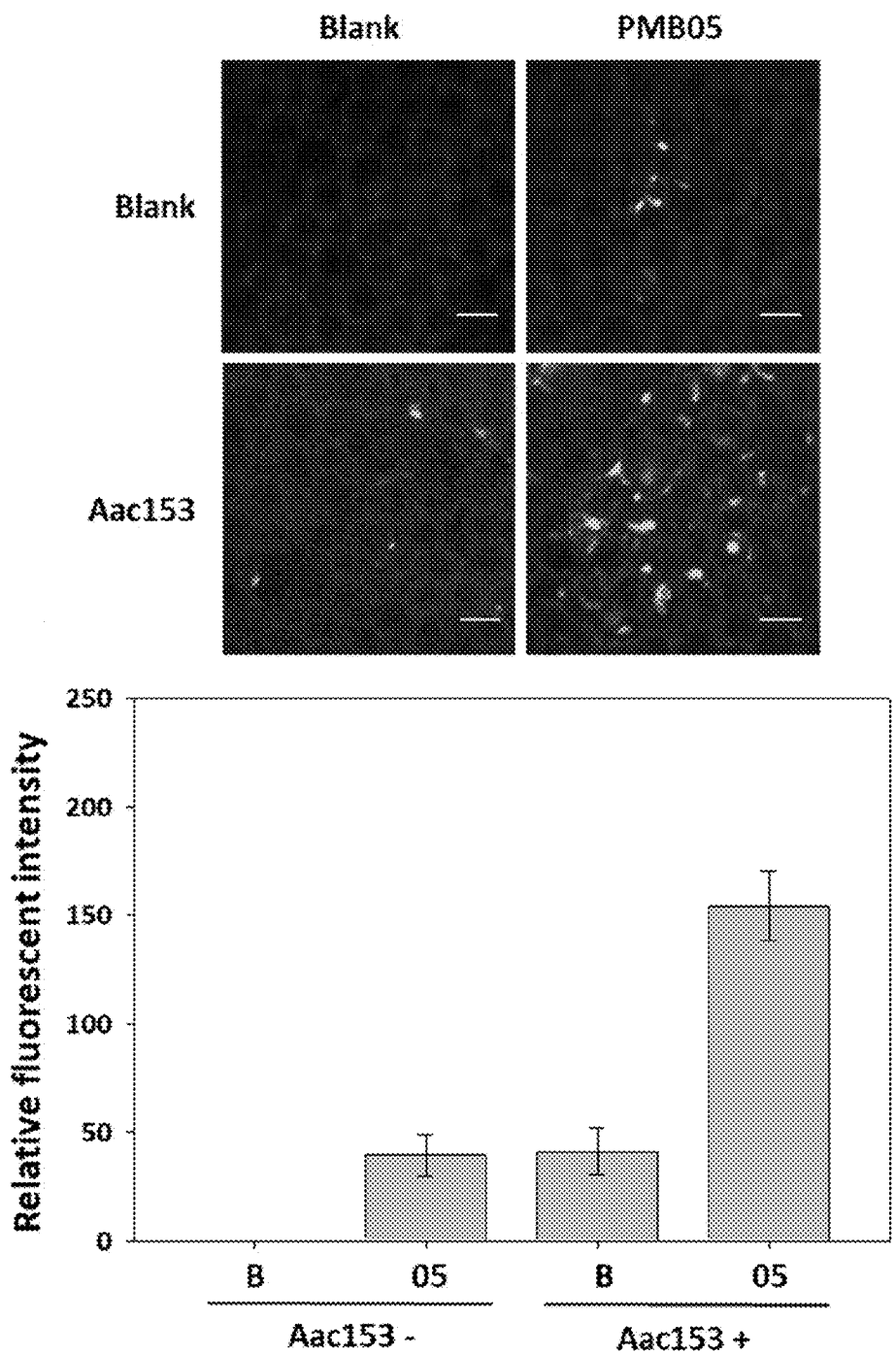
FIG. 18 shows the deposition of callose intensified by strain PMB05 cell suspension after the inoculation of *Acidovorax citrulli* in watermelon.

The results are shown in FIG. 18. After 8 hours from the treatment, observe the leaves only treated with Aac153 under a florescence microscope and there is a trace of callose decomposition. In contrast to the control group, there is an increasing trend of callose deposition in the group of leaves treated with both Aac153 and PMB05. Furthermore, in the group of leaves only treated with PMB05, the callose deposition is very weak. After quantification of the fluorescence signals of callose, use the group only treated with water (labelled as B, Aac153−) as the control group to standardize all the quantified signals. The results demonstrate that the relative fluorescence intensity of control groups solely treated with Aac153 or PMB05 is 41.3 times and 39.7 times respectively. The relative fluorescence intensity of experimental group treated with both Aac153 and PMB05 increases to 154.3 times. It shows that PMB05 can significantly increase the deposition of callose which is induced by the watermelon's detection of *Acidovorax citrulli* strain Aac153.

Example 13: ROS Deposition Intensification after the Detection of Pathogen-Associated Molecular Patterns Flg22$_{Pst}$ in Plant The current example further evaluates the intensification by PMB05 treatment in immune response of ROS deposition after detection of pathogen-associated molecular patterns by plant cells. The pathogen-associated molecular pattern used is flg22$_{Pst}$ (originated from *Pseudomonas syringae* pv. *tabaci*), which can be detected by various species of plants; the plants used are leaves of watermelon and *Arabidopsis*.

First, mix 1 μM of flg22$_{Pst}$ and PMB05 bacterial cell suspension at OD600 value 0.3 in the volume ratio of 1:1. The inoculation by injection method is same as the method in aforementioned embodiment 11. To study the production of $H_2O_2$, 3 leaves from the plants are collected randomly at 1 hour after inoculation. The methods of observation and analysis are the same as the methods in embodiment 11. Each test accesses 3 leaves and 3 repeat tests are performed, then use Tukey-Kramer method (p<0.05) for statistically analyzing the data obtained from one of the repeat test.

Figure 19:
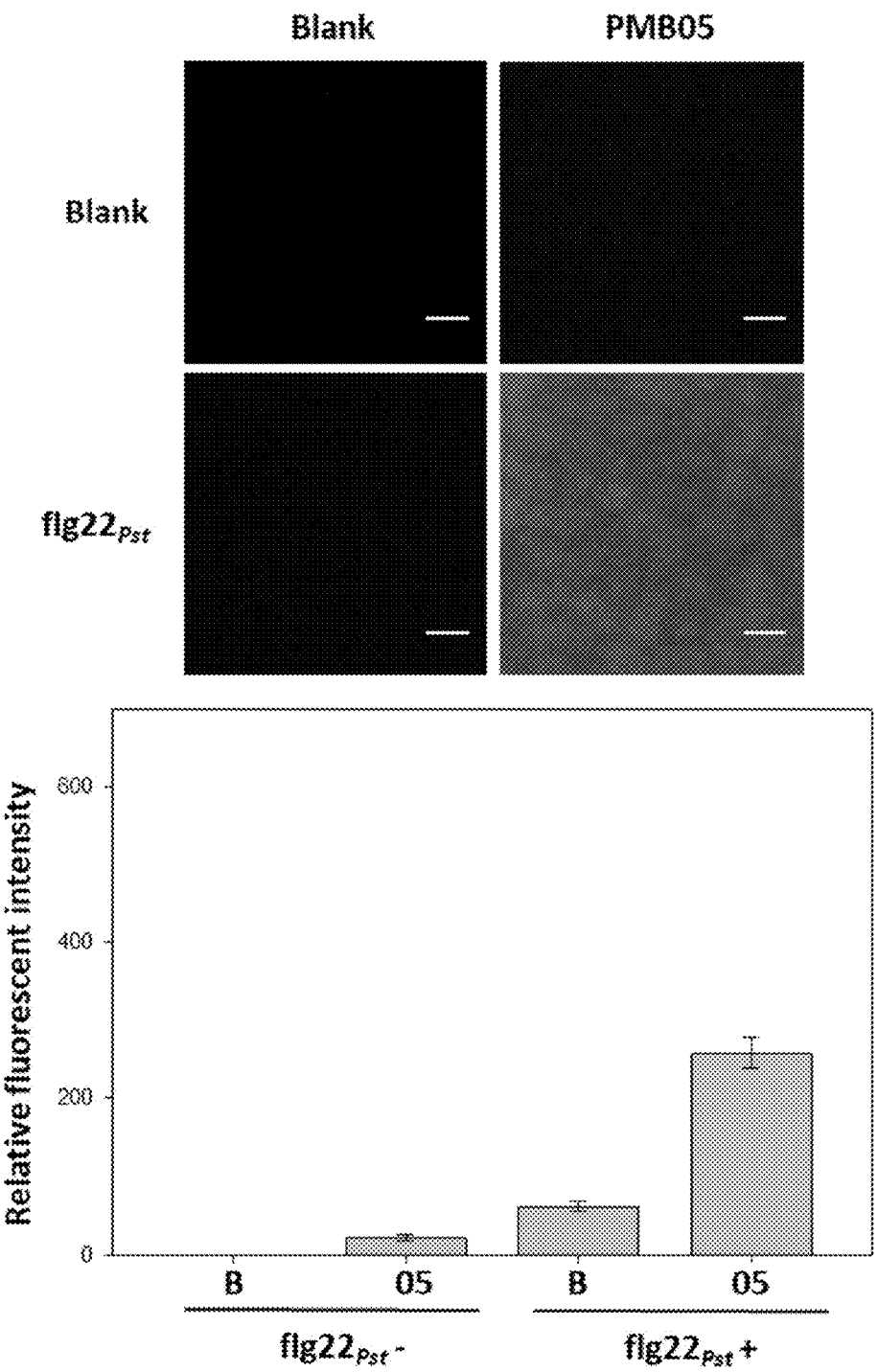
FIG. 19 shows the deposition of ROS intensified by strain PMB05 cell suspension after the inoculation of flg22$_{Pst}$ in watermelon.

The results of treated watermelon plants are shown in FIG. 19. After 1 hour from treatment, observe the group of leaves only treated with flg22$_{Pst}$ under a fluorescence microscope and there is a trace amount of $H_2O_2$ production; in the group treated with both flg22$_{Pst}$ and PMB05, there is an increasing trend of $H_2O_2$ production, which is significantly higher than that of the group only treated with flg22$_{Pst}$. Furthermore, in the group only treated with PMB05, there is only a trace amount of $H_2O_2$ production. After quantification of the fluorescence signals of $H_2O_2$, set the control group only treated with water (labelled as flg22$_{Pst}$−, B) as the standard. The relative fluorescence intensity of group solely treated with flg22$_{Pst}$ is increased by 59.0 times, whereas the relative fluorescence intensity of group solely treated with PMB05 is 22.0 times. In contrast to the above groups, the relative fluorescence intensity of experimental group treated with both Aac153 and PMB05 is increased by 540.5 times. It shows that PMB05 can significantly intensify the rapid production of $H_2O_2$ which is induced by the plant's detection of flg22$_{Pst}$.

Figure 26:
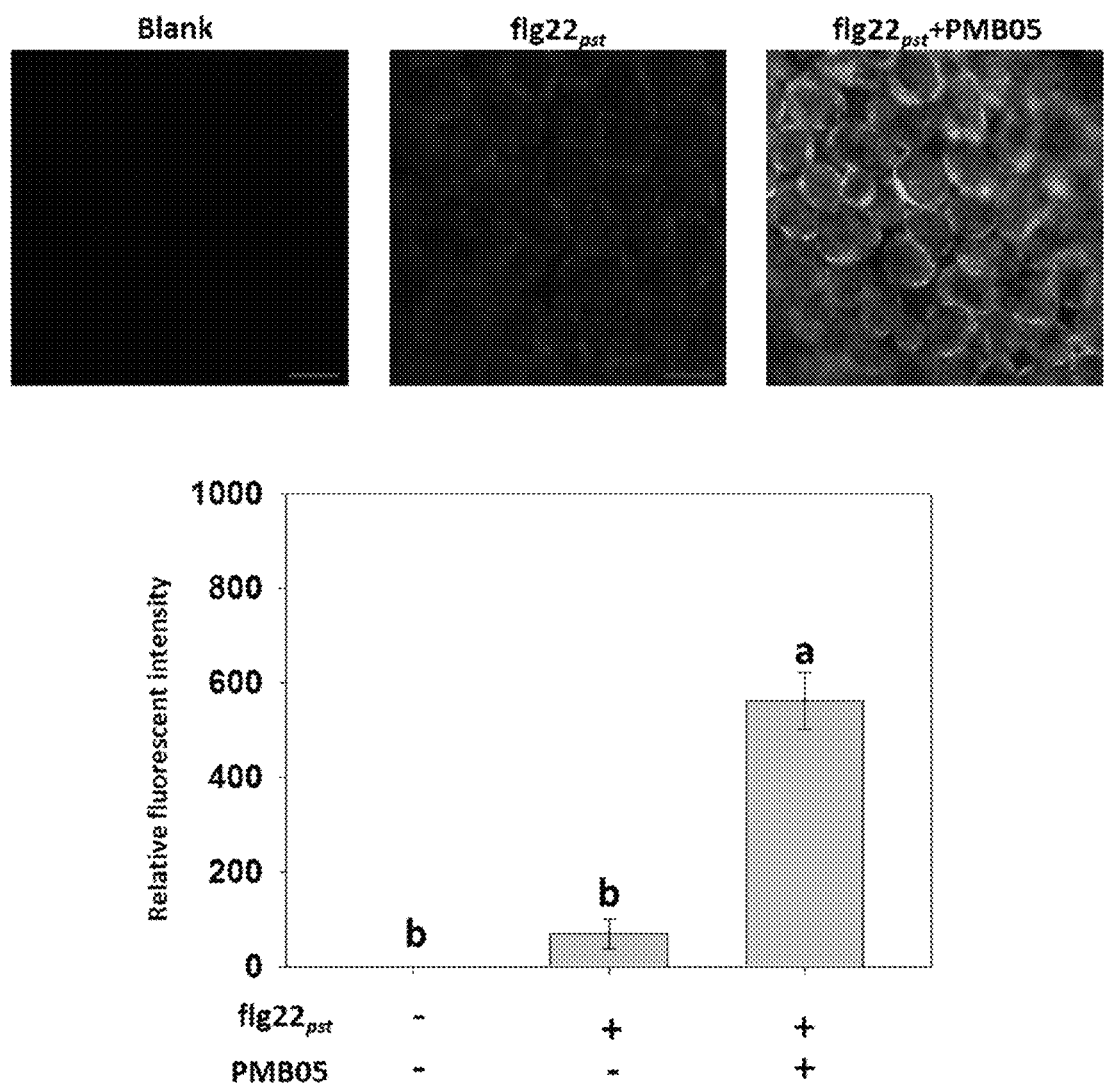
FIG. 26 shows the deposition of ROS intensified by strain PMB05 cell suspension after the inoculation of flg22$_{Pst}$ in *Arabidopsis*.

The results of treated *Arabidopsis* plants are shown in FIG. 26. After 1 hour from the treatment, observe the group of leaves only treated with flg22$_{Pst}$ under a fluorescence microscope and there is a trace amount of $H_2O_2$ production; in the group treated with both flg22$_{Pst}$ and PMB05, there is an increasing trend of $H_2O_2$ production.

Example 14: Callose Deposition Intensification after the Detection of Pathogen-Associated Molecular Patterns Flg22$_{Pst}$ in Plant The current example further evaluates the intensification by PMB05 treatment in immune response of callose deposition after detection of pathogen-associated molecular patterns by plant cells. The pathogen-associated molecular pattern used is flg22$_{Pst}$ (originated from *Pseudomonas syringae* pv. *tabaci*), which can be detected by various species of plants; the plants used are leaves of watermelon and *Arabidopsis*.

First, mix 1 μM of flg22$_{Pst}$ and PMB05 bacterial cell suspension at OD600 value 0.3 in the volume ratio of 1:1, and inoculate the leaves using the inoculation method in aforementioned embodiment 12. To study the deposition of callose, 3 leaves from the plants are collected randomly at 8 hours after inoculation. The methods of observation and analysis are the same as the methods in embodiment 12. Each test accesses 3 leaves and 3 repeat tests are performed, then use t-test (p<0.05) which can assess two different treatment groups for statistically analyzing the data obtained from one of the repeat test.

Figure 20:
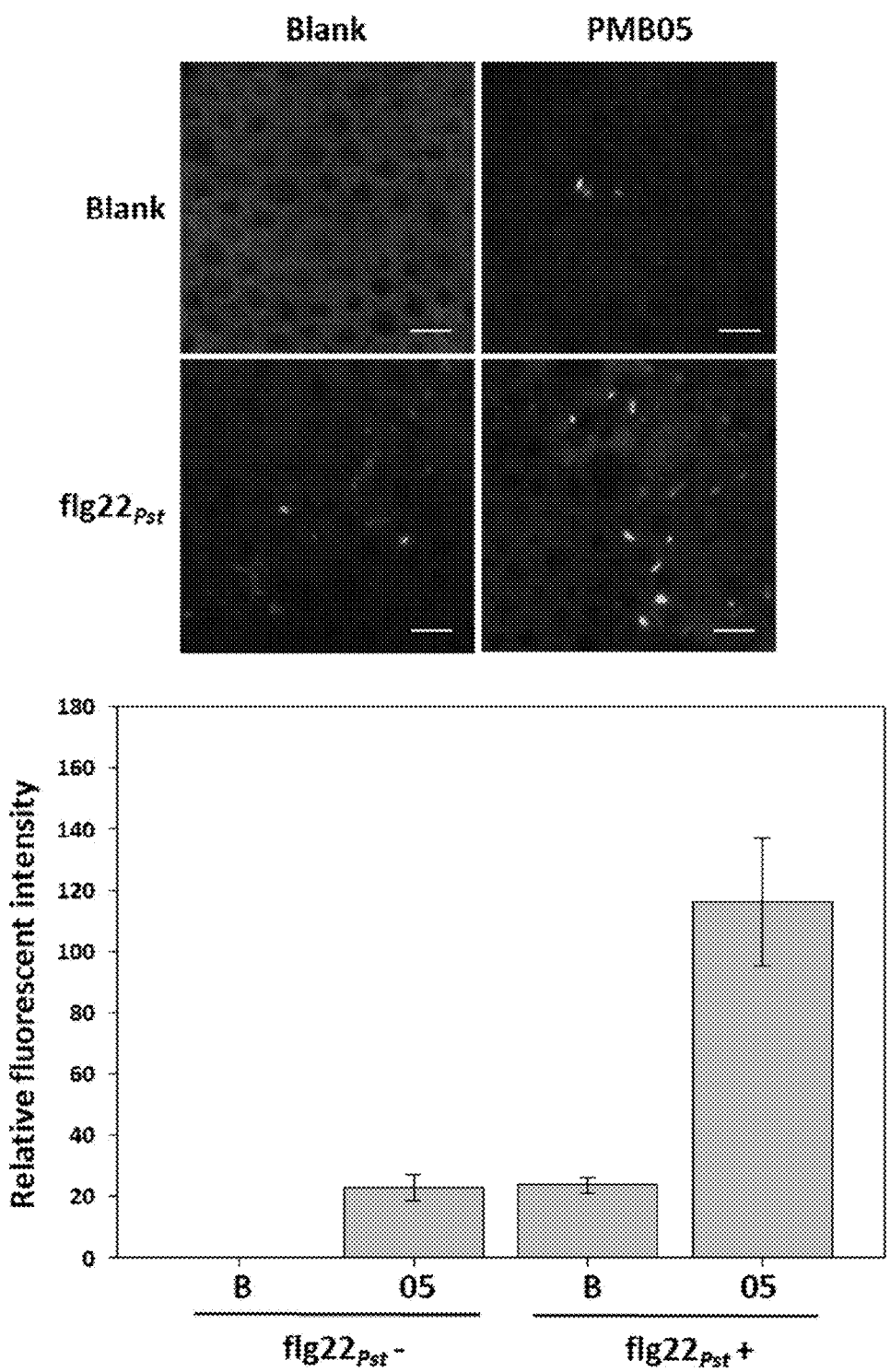
FIG. 20 shows the deposition of callose intensified by strain PMB05 cell suspension after the inoculation of flg22$_{Pst}$ in watermelon.

The results of treated watermelon plants are shown in FIG. 20. After 8 hours from treatment, observe the group of leaves only treated with flg22$_{Pst}$ under a fluorescence microscope and there is a trace amount of callose deposition; in the group treated with both flg22$_{Pst}$ and PMB05, there is an upward trend of callose deposition. Moreover, in the group only treated with PMB05, the callose deposition is very weak. After quantifying the fluorescence signals of callose, set the control group only treated with water (labelled as B, flg22$_{Pst}$−) as the standard. The relative fluorescence intensity of groups solely treated with flg22$_{Pst}$ or PMB05 are increased to 23.7 times and 23.0 times respectively; the relative fluorescence intensity of experimental group treated with both Aac153 and PMB05 is increased to 116.0 times. It shows that PMB05 can significantly intensify the deposition of callose which is induced by the plant's detection of flg22$_{Pst}$.

Figure 27:
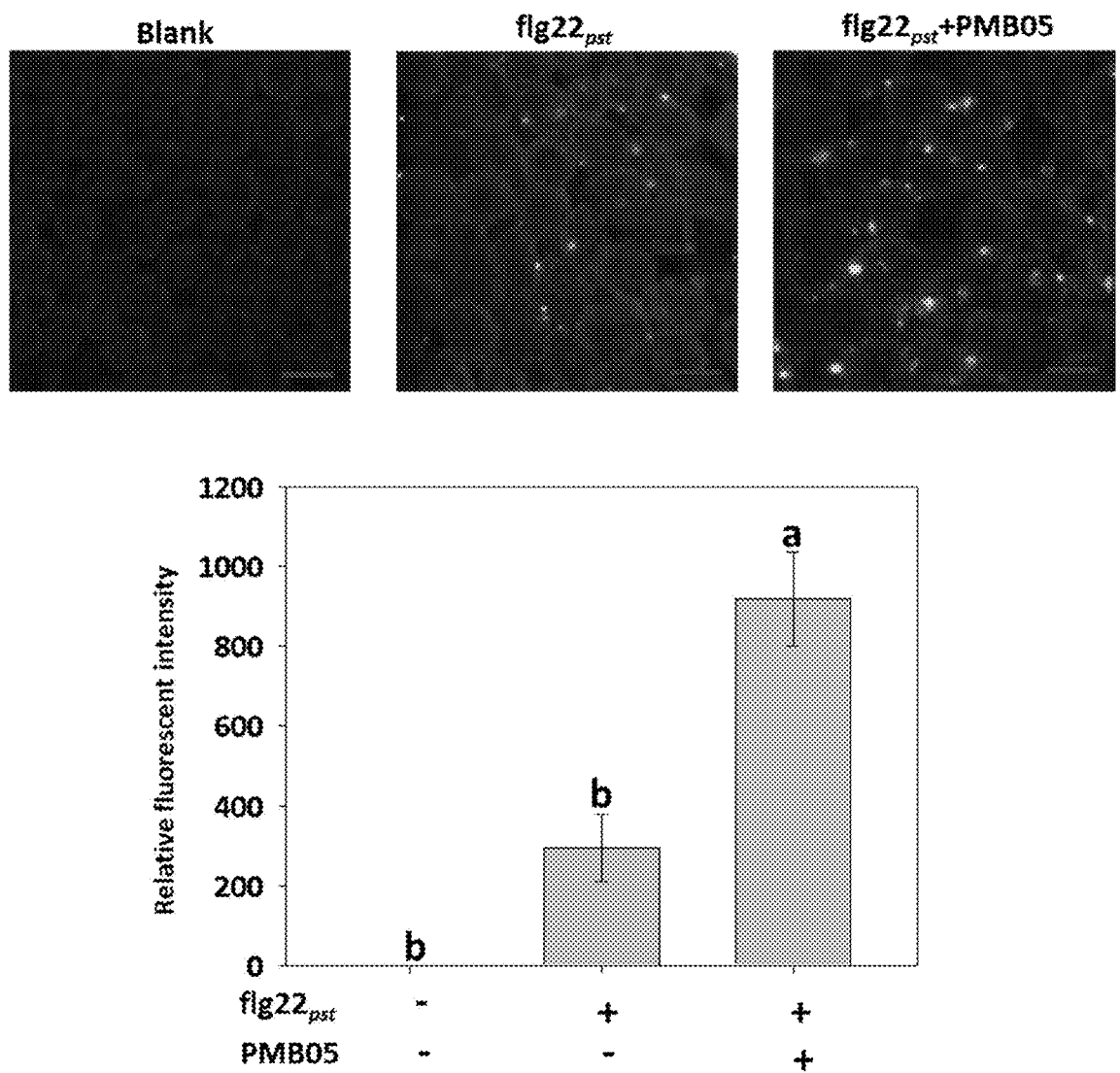
FIG. 27 shows the deposition of callose intensified by strain PMB05 cell suspension after the inoculation of flg22$_{Pst}$ in *Arabidopsis*.
Figure 28:
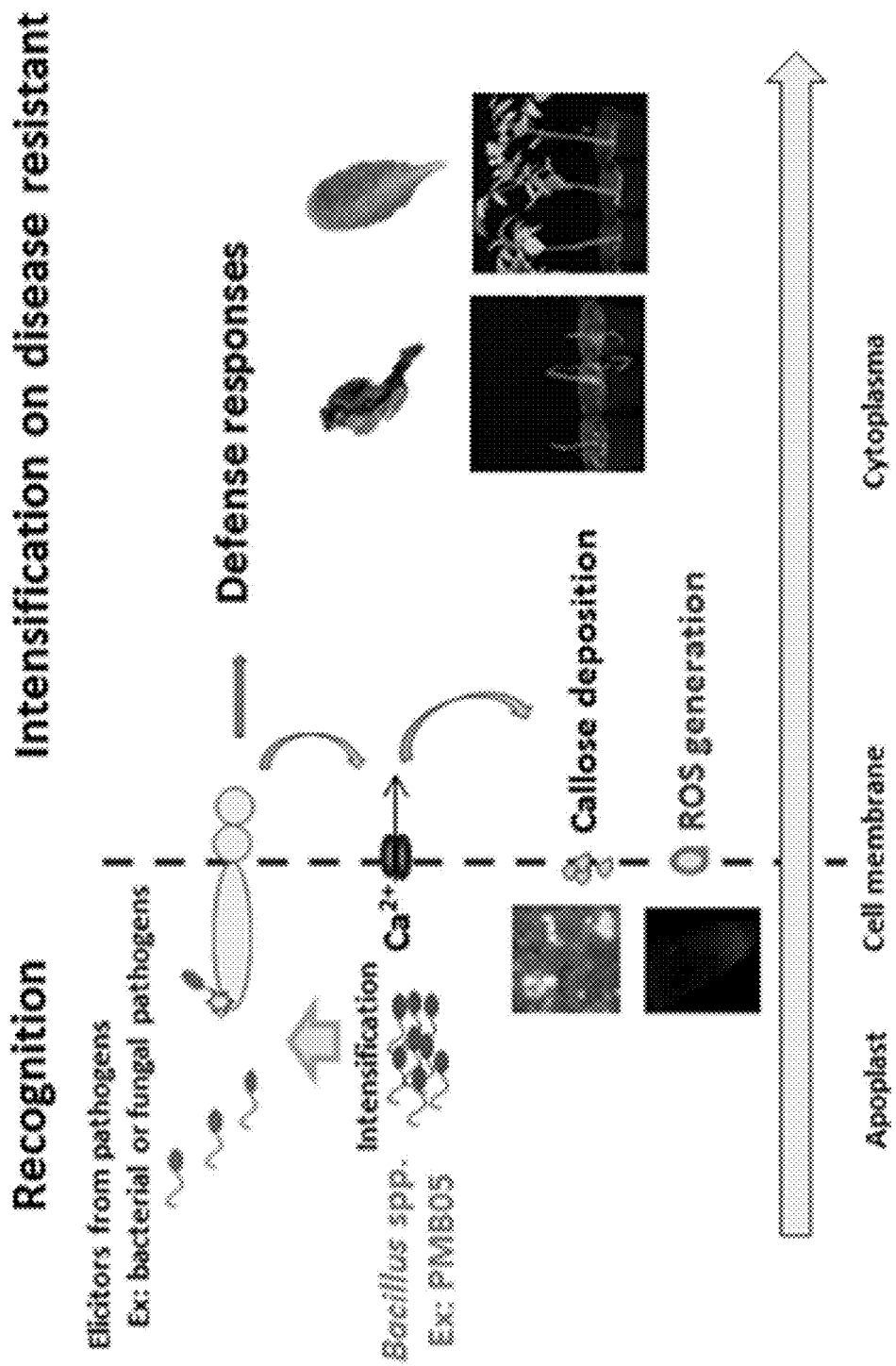
FIG. 28 illustrates the mechanism of strain PMB05 boosting plant immune responses.

The results of treated *Arabidopsis* plants are shown in FIG. 27. Observe the group of leaves only treated with flg22$_{Pst}$ under a fluorescence microscope and there is a trace amount of callose deposition; in the group treated with both flg22$_{Pst}$ and PMB05, there is a rapidly increasing trend of the amount of callose deposition.

Example 15: Effect for Controlling Bacterial Soft Rot

The current example is to evaluate the control efficacies against bacterial soft rot (*Pectobacterium carotovorum* subsp. *Carotovorum*) on *Arabidopsis* after treated with strain PMB05 cell suspension. For the strain PMB05 cell suspension in this embodiment, apart from changing the incubation condition of nutrient broth to incubate for 24 hours at 28° C., and substituting the liquid for adjusting the cell suspension concentration from sterile $H_2O$ to Tris-HCl buffer (pH 7.5), other conditions are the same as the foresaid embodiments. The strain used in the following embodiment for bacterial soft rot is Ecc17. Then purify the strain in NA culture medium, massively amplified he culture medium overnight and adjust the concentration of the bacterial cell suspension to OD600 value 0.3 with Tris-HCl buffer (pH 7.5). The cell suspension is then diluted 100 times, and the bacterial concentration is approximately $10^6$ CFU/ml. Mix the prepared Ecc17 bacterial solution ($10^6$ CFU/ml) with PMB05 bacterial cell suspension in the volume ratio of 1:1, and the mixture is inoculated to leaves of *Arabidopsis*. After that, bag the leaves and place them in the growth chamber at 22° C. Observe the disease severity of the plants after 24 hours. Disease severity is divided in to 4 levels:
1: 0-25% soft decay of the leaf;
2: 25-50% soft decay of the leaf;
3: 50-75% soft decay of the leaf;
4: 75-100% soft decay of the leaf.

Calculate the results with the formula below:

$$[(1 \times N_1 + 2 \times N_2 + 3 \times N_3 + 4 \times N_4)/(4 \times N)] \times 100\%$$

Figure 25:
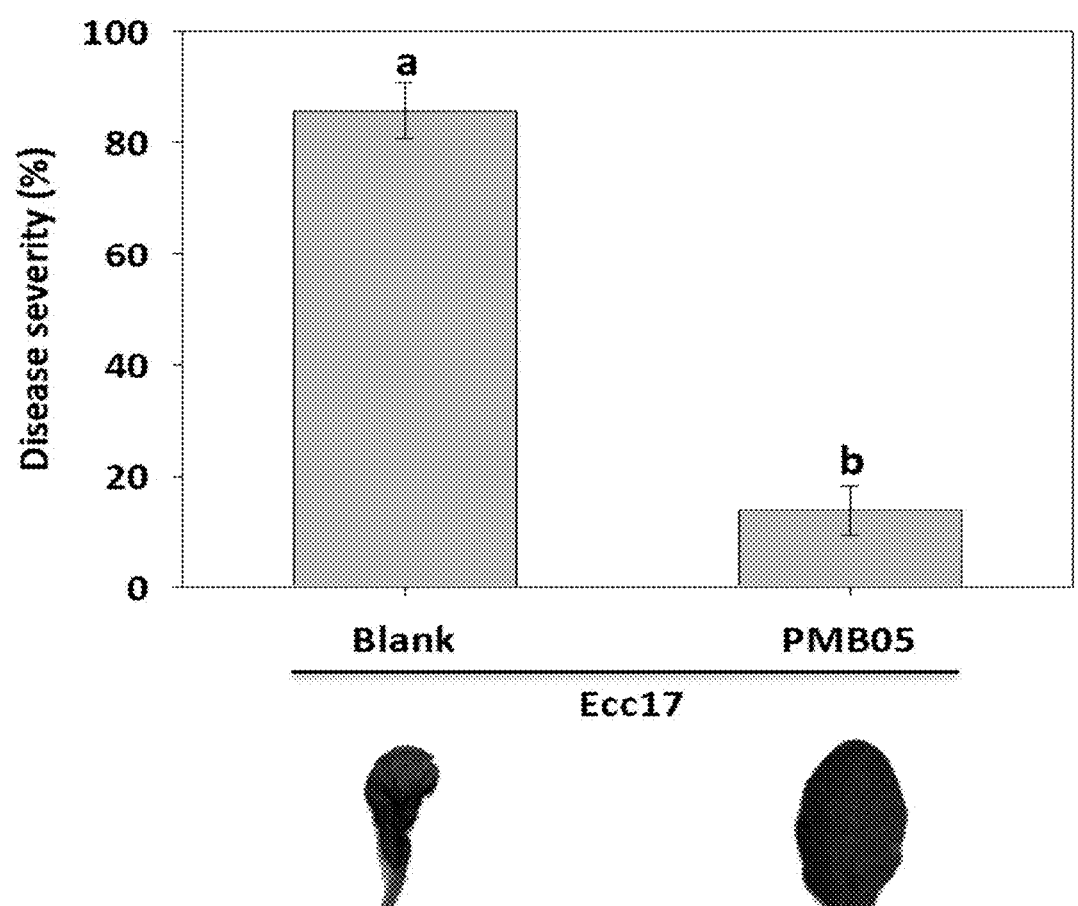
FIG. 25 shows the control efficacies of strain PMB05 against bacterial soft rot on *Arabidopsis*.

The outcomes are the disease severity of bacterial soft rot, and statistically analyze the results. For the control group, replace PMB05 bacterial cell suspension with Tris-HCl buffer (pH 7.5) and inoculate it to the leaves by injection. The results are shown in FIG. 25. At 24 hours after inoculation, symptoms of bacterial soft rot are observed on the leaves of the group only inoculated with bacterial soft rot strain Ecc17 (labelled as Blank). In the group co-treated with Ecc17 and PMB05, no obvious symptoms are observed on the leaves after 24 hours. Further, the calculation of disease severity shows the disease severity of the group co-treated with Ecc17 and PMB05 is significantly lower than that of the control group solely treated with Ecc17.

Example 16: Effectiveness of Promoting Plant Growth (Strawberry)

The current example is to evaluate the effectiveness of strain PMB05 in promoting plant growth. Prepare strain PMB05 cell suspension at OD600 value 0.3, and pour 15 ml strain PMB05 cell suspension into each pathogen-free seedling that has been acclimated for one week. Process 5 plants in total and each plant is treated every week. Observe the plant growth parameters like number of leaves and fresh weight of the plant.

Analyse the number of leaves, plant height and fresh weight of pathogen-free strawberry seedlings after treatment with strain PMB05 cell suspension. The results are shown in CHART 3, wherein PMB05 treatment can increase the fresh weight of strawberry plant.

TABLE 3

| Group | Number of Leaves | Plant Height (cm) | Fresh Weight (g) |
|---|---|---|---|
| Control Group | 5.75 a* | 7.03 a | 2.07 a |
| PMB05 | 7.75 ab | 7.55 a | 3.84 b |

Example 17: Effectiveness of Promoting Plant Growth (Watermelon)

The current example is to evaluate the effectiveness of practical application of strain PMB05 in promoting plant growth in the field. Prepare strain PMB05 cell suspension at OD600 value 0.3 (the bacterial concentration is approximately $10^7$ CFU/ml), and mix the cell suspension with cultivated substrates in the volume ratio of 1:10. Then, fill a soft pot of 9 cm diameter with the cultivated soil mixed with strain PMB05 cell suspension. Finally, plant a single seed in the cultivated soil that contains strain PMB05, and 10 repeat in one test. After cultivating the plants in greenhouse for 14 days, apply the strain PMB05 cell suspension with same proportion to each plant by hand watering method. Analyse the parameters like fresh weight and leaf surface area at Day 28.

To measure the fresh weight of plant, remove the plant from the soil level and weigh the plant. Each test access 5 plants and 3 repeat tests are performed. To calculate the plant leaf surface area, collect the second leaf (excluding the cotyledon) from the watermelon plant. After collecting the leaves, use a camera to convert the leaf to an image, and calculate the leaf surface area by bioimaging software ImageJ. Each test access 5 plants and 3 repeat tests are performed. Then use Tukey-Kramer method (p<0.05) for statistically analyzing the data obtained from one of the repeat test.

Figure 21:
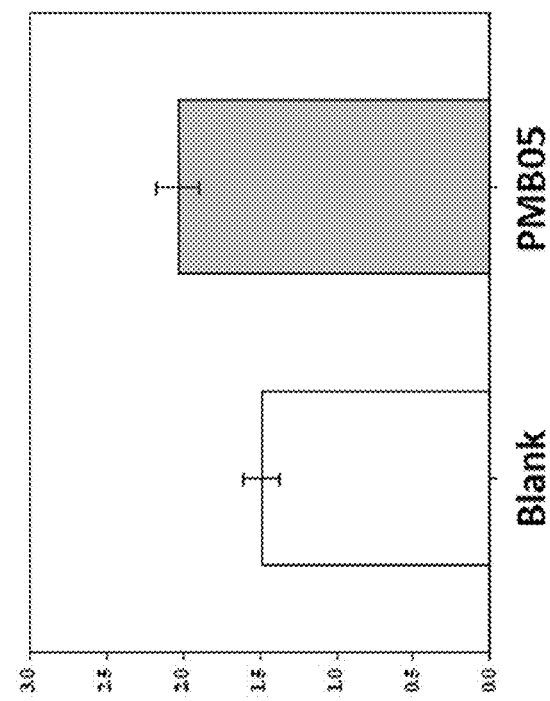
FIG. 21 shows the effectiveness of strain PMB05 in promoting watermelon plant growth.
Figure 21:
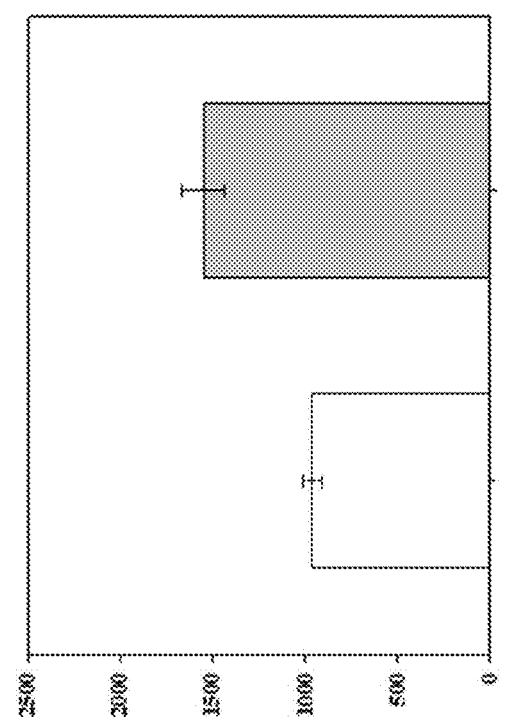

The results are shown in FIG. 21. In the analysis of leaf surface area, the average leaf surface area of control group is 960 mm, while the average leaf surface area of leaf treated with PMB05 is 1548 mm. It shows that PMB05 has a significant enhancing effect since the leaf surface area increases by approximately 61.3%. In the measurement of plant fresh weight, the fresh weight of group treated with PMB05 is also significantly increased. The fresh weight of control group is 1.49 g, while the fresh weight of group treated with PMB05 is 2.03 g, increasing by approximately 36.2%.

As described in the aforementioned embodiments and their effects, the *Bacillus amyloliquefaciens* strain PMB05 of the present invention is effective in intensifying the plant immune responses induced by detection of fungi and/or bacteria, thus boosting the disease resistance of plants. Since strain PMB05 has the potential of turning into a commodified biological control agent and can be extensively used to control plant diseases in industries like food crops industry, floral industry and fruit tree industry, it has a high industrial applicability.

Moreover, the present invention is the first disclosure of a *Bacillus amyloliquefaciens* strain that can immune responses of plants after the detection of the bacteria. The technical means are not seen in any other inventions in this technical field, hence the present invention is novel and innovative.

The above terms and explanations are included but not limited to demonstrate embodiments of the invention. Accordingly, this invention includes all embodiments, modifications and variations that contain technical features of the present invention without departing from the spirit and scope of the invention, and the scope thereof is determined by the appended claims.

What is claimed is:

1. A method of reducing the severity of or treating a plant infected with bacterial fruit blotch or bacterial soft rot comprising contacting the plant with a composition comprising *Bacillus amyloliquefaciens* strain PMB05, thereby increasing a pathogen-associated molecular pattern (PAMP)-triggered immune response of the plant induced by detection of bacteria,
    wherein a representative sample of said strain was deposited with the China Center for Type Culture Collection under Accession No. CCTCC M 2018075;
    wherein said plant is a watermelon plant or *Arabidopsis* plant;
    wherein said PAMP-triggered immune response comprises production of reactive oxygen species (ROS) and/or deposition of callose; and wherein a concentration of *Bacillus amyloliquefaciens* strain PMB05 in the composition is equal to an optical density in a culture of at least 0.3 OD600.

2. The method of claim 1, wherein the *Bacillus amyloliquefaciens* strain PMB05 promotes plant growth.

3. The method of claim 1, wherein said *Bacillus amyloliquefaciens* strain PMB05 is applied to a leaf of the plant.

4. A method of increasing a PAMP-triggered immune response of a watermelon plant or *Arabidopsis* plant induced by detection of bacterial fruit blotch bacteria or bacterial soft rot bacteria, comprising contacting the watermelon plant or *Arabidopsis* plant with a composition comprising *Bacillus amyloliquefaciens* strain PMB05, wherein a representative sample of said strain was deposited with the China Center for Type Culture Collection under Accession No. CCTCC M 2018075, thereby increasing said PAMP-triggered immune response, and wherein a concentration of *Bacillus amyloliquefaciens* strain PMB05 in the composition is equal to an optical density in a culture of at least 0.3 OD600.

5. The method of claim 4, wherein said PAMP-triggered immune response comprises production of reactive oxygen species (ROS) and/or deposition of callose.

6. The method of claim 4, wherein the said *Bacillus amyloliquefaciens* strain PMB05 is prepared in the form of culture filtrate and/or cell suspension, as an active agent of a microbial agent.

7. The method of claim 4, wherein said *Bacillus amyloliquefaciens* strain PMB05 is applied to a leaf of the plant.

\* \* \* \* \*